United States Patent
Kuramoto

(10) Patent No.: US 10,003,774 B2
(45) Date of Patent: Jun. 19, 2018

(54) IMAGE PROCESSING DEVICE AND METHOD FOR OPERATING ENDOSCOPE SYSTEM

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 350 days.

(21) Appl. No.: 14/823,053

(22) Filed: Aug. 11, 2015

(65) Prior Publication Data
US 2016/0006993 A1 Jan. 7, 2016

Related U.S. Application Data

(63) Continuation of application No. PCT/JP2014/052247, filed on Jan. 31, 2014.

(30) Foreign Application Priority Data

Feb. 27, 2013 (JP) ................................ 2013-037782

(51) Int. Cl.
*A61B 1/04* (2006.01)
*H04N 9/04* (2006.01)
(Continued)

(52) U.S. Cl.
CPC ............. *H04N 9/04* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS

| 2008/0306338 A1 | 12/2008 | Yamazaki et al. |
| 2012/0154566 A1 | 6/2012 | Kaku |
| 2012/0197076 A1* | 8/2012 | Minetoma .......... A61B 1/00009 600/109 |

FOREIGN PATENT DOCUMENTS

| JP | 2003-93336 A | 4/2003 |
| JP | 2003093336 A * | 4/2003 |

(Continued)

OTHER PUBLICATIONS

International Preliminary Report on Patentability, issued in PCT/JP2014/052247, dated May 12, 2015.
(Continued)

*Primary Examiner* — James M Anderson, II
(74) *Attorney, Agent, or Firm* — Birch, Stewart, Kolasch & Birch, LLP

(57) ABSTRACT

A base image includes a B image signal in which ductal structure is brighter than mucous membrane and capillary vessels are darker than the mucous membrane. The B image signal is subjected to a frequency filtering process for extracting frequency components including the ductal structure and the capillary vessels. Thereby, a structure-extracted image signal, in which a pixel value of the ductal structure is a positive value and a pixel value of the capillary vessels is a negative value, is generated. Based on the structure-extracted image signal, a display controlling image to be used for enhancing display of the ductal structure and suppressing display of the capillary vessels is generated. The base image is combined with the display controlling image to obtain a display-controlled image in which the display of the ductal structure is enhanced and the display of the capillary vessels is suppressed.

18 Claims, 21 Drawing Sheets

(51) Int. Cl.
 *G02B 23/24* (2006.01)
 *G02B 23/26* (2006.01)
 *A61B 1/00* (2006.01)
 *G06K 9/46* (2006.01)
 *H04N 5/225* (2006.01)
 *H04N 5/232* (2006.01)
 *H04N 5/262* (2006.01)
 *H04N 5/265* (2006.01)
 *H04N 9/79* (2006.01)

(52) U.S. Cl.
 CPC ......... *G02B 23/2484* (2013.01); *G02B 23/26* (2013.01); *G06K 9/46* (2013.01); *G06K 9/4652* (2013.01); *H04N 5/2256* (2013.01); *H04N 5/23293* (2013.01); *H04N 5/265* (2013.01); *H04N 5/2628* (2013.01); *H04N 9/7908* (2013.01); *A61B 1/04* (2013.01); *H04N 2005/2255* (2013.01)

(56) References Cited

FOREIGN PATENT DOCUMENTS

| JP | 2012-125461 A | 7/2012 |
| JP | 2012-152332 A | 8/2012 |
| JP | 2012-152459 A | 8/2012 |
| JP | 2012152332 A * | 8/2012 |
| JP | 5057675 B2 | 10/2012 |

OTHER PUBLICATIONS

International Search Report, issued in PCT/JP2014/052247, dated May 13, 2014.
Written Opinion of the International Searching Authority, issued in PCT/JP2014/052247, dated May 13, 2014.

* cited by examiner

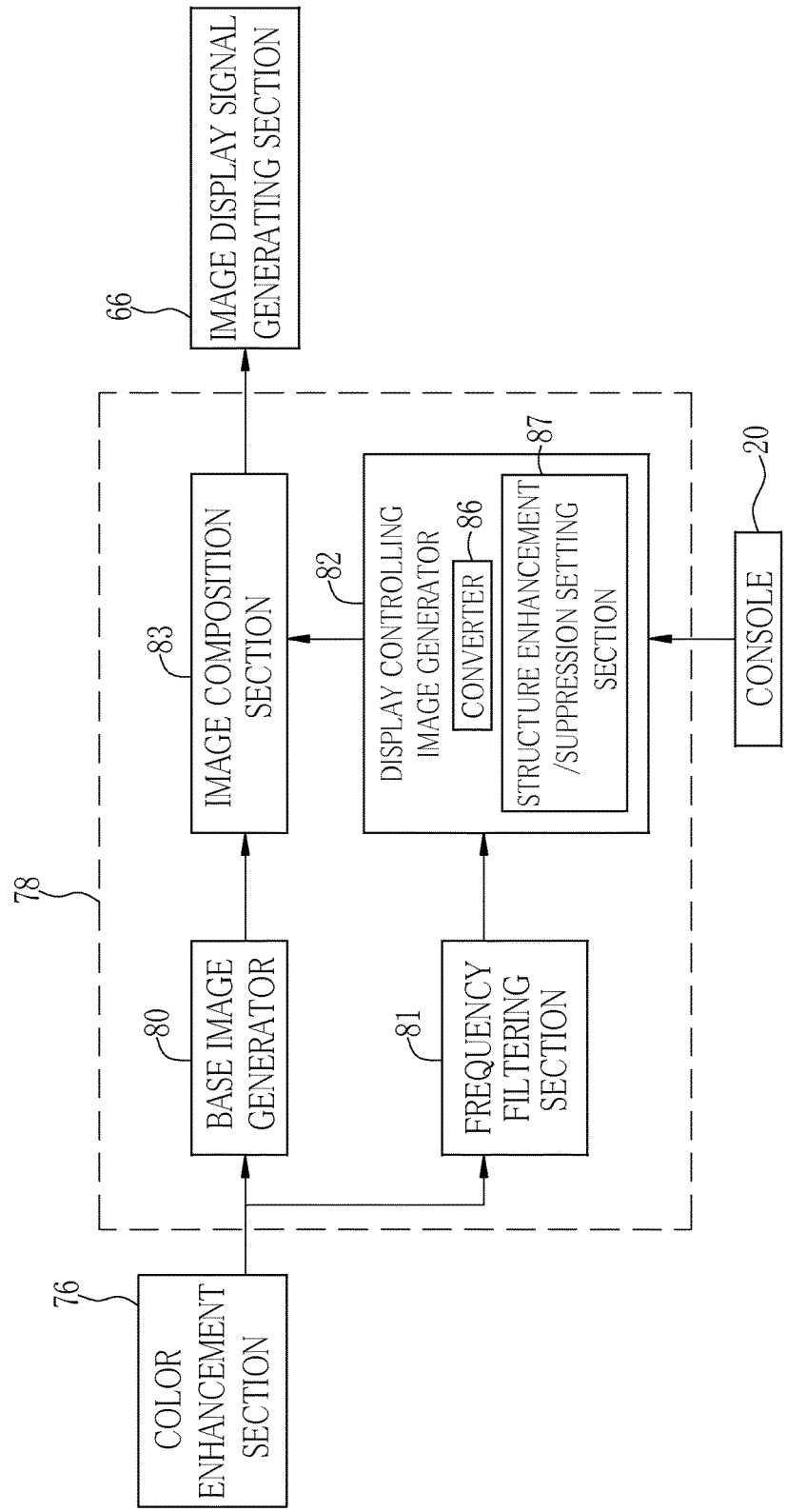

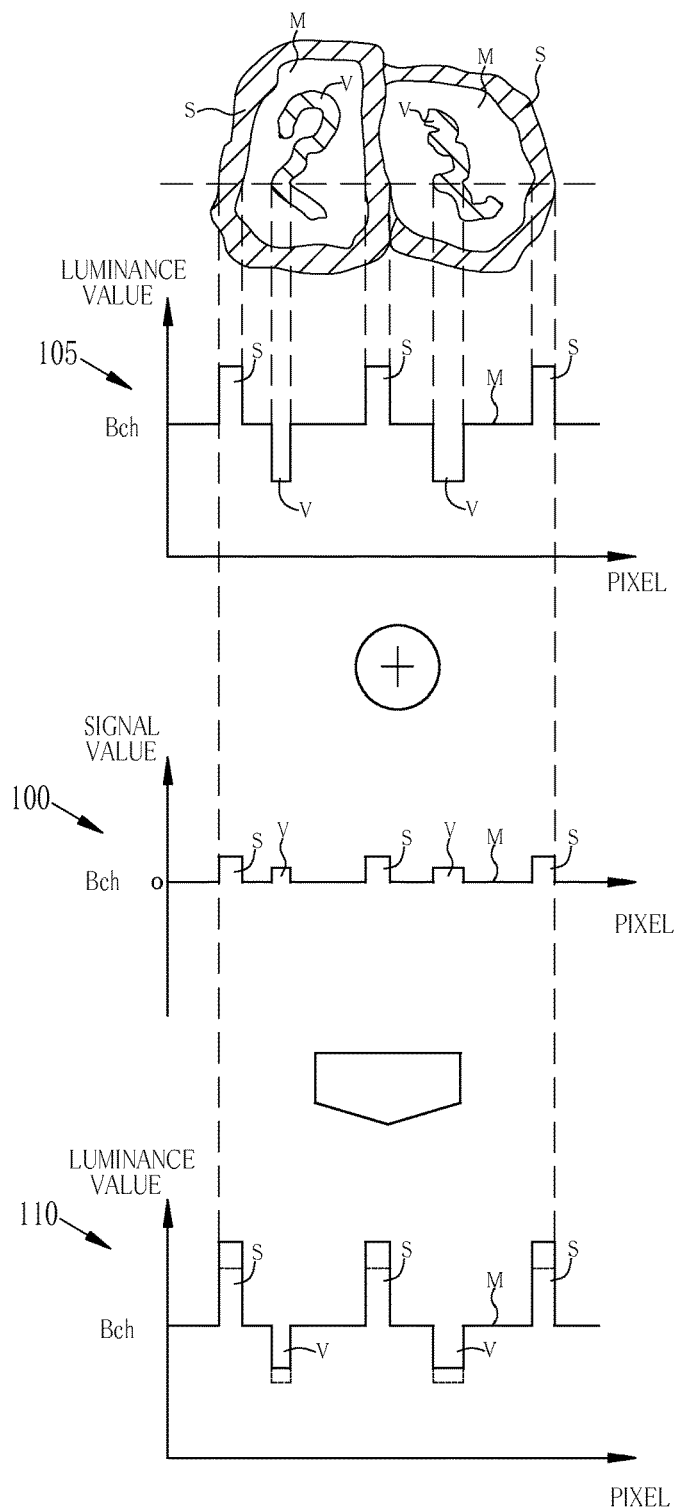

IMAGE PROCESSING DEVICE AND METHOD FOR OPERATING ENDOSCOPE SYSTEM

CROSS-REFERENCE TO RELATED APPLICATIONS

This application is a Continuation of PCT International Application No. PCT/JP2014/052247 filed on Jan. 31, 2014, which claims priority under 35 U.S.C § 119 (a) to Japanese Patent Application No. 2013-037782 filed Feb. 27, 2013. The above application is hereby expressly incorporated by reference, in its entirety, into the present application.

BACKGROUND OF THE INVENTION

1. Field of the Invention

The present invention relates to an image processing device and a method for operating an endoscope system, for performing diagnoses based on observation of a ductal structure and capillary vessels.

2. Description Related to the Prior Art

Diagnoses using endoscope systems are widely performed in current medical care. The endoscope system includes a light source device, an electronic endoscope, and a processor device. Observation of an inside of an observation object is performed using the endoscope system. Such observation includes screening observation and magnified observation. In the screening observation, a potential lesion, which is a site with a high possibility of being a lesion, such as a brownish area or redness is detected from a far view. The magnified observation is performed in the case where such a potential lesion is detected. In the magnified observation, a zooming lens is used to magnify the potential lesion so as to perform careful examination of the potential lesion. As the magnified observation, in recent years, "VS classification" in which diagnoses based on observation of a fine membrane structure are performed, has been conducted.

In the "VS classification", diagnoses based on observation of capillary vessels in a surface layer of a mucous membrane and diagnoses based on observation of a microstructure of the surface layer of the mucous membrane are separately performed. Therefore, it is required to enhance the display of both of the capillary vessels and the microstructure. For the display enhancement, for example, it is possible to extract blood vessel portions from a predetermined image and enhance only the display of the extracted blood vessel portions, as disclosed in United States Patent Application Publication No. 2012/0197076 corresponding to Japanese Patent Laid-Open Publication No. 2012-152459. According to United States Patent Application Publication No. 2012/0197076, since the display of the blood vessel portions is enhanced while the microstructure other than the blood vessel portions remains to be displayed without being disappeared, observation of both of the capillary vessels and the microstructure becomes facilitated. Further, since each of the capillary vessels and the microstructure has mid-frequency components and high-frequency components, it is possible to enhance the display of both of the capillary vessels and the microstructure by performing high-pass filtering as disclosed in United States Patent Application Publication No. 2008/0306338 corresponding to Japanese Patent No. 5057675.

In the recent "VS classification", it has become clear that the existence of the blood vessels hinders accurate diagnoses of the microstructure in performing diagnoses based on observation of the microstructure. For example, in the case where blood vessels are contained in part of the microstructure which has been already disappeared, an area surrounded by the blood vessels may look like the microstructure. In such a case, possibility of misdiagnosis is increased. Consequently, it is required to generate and display an endoscope image, in which one of the capillary vessels and the microstructure does not impair the visual recognition of the other of them, by performing display control. In the display control, the display of one of the capillary vessels and the microstructure is enhanced and the display of the other of them is suppressed (i.e., selective enhancement/suppression of the display of the capillary vessels and the microstructure is performed), such that the visual recognition of the capillary vessels and the visual recognition of the microstructure are different from each other.

Although United States Patent Application Publication No. 2012/0197076 discloses selective enhancement/suppression of the display of the superficial blood vessels and the deep blood vessels, United States Patent Application Publication No. 2012/0197076 does not disclose selective enhancement/suppression of the display of the capillary vessels and the microstructure. Further, although United States Patent Application Publication No. 2008/0306338 discloses a filtering process capable of enhancing the display of both of the microstructure and the capillary vessels, it is impossible to perform selective enhancement/suppression of the display of the capillary vessels and the microstructure by the filtering process disclosed in United States Patent Application Publication No. 2008/0306338.

SUMMARY OF THE INVENTION

In view of the foregoing, an object of the present invention is to provide an image processing device and a method for operating an endoscope system, capable of generating an endoscope image in which one of capillary vessels and microstructure does not impair visual recognition of the other of them, even in the case where diagnoses are separately performed on the capillary vessels and the microstructure.

To achieve the above object of the present invention, an image processing device of the present invention includes an image signal generator, a base image generator, a structure-extracted image generator, a display controlling image generator, and an image compositor. The image signal generator generates image signals of a plurality of colors by capturing an image of a mucous membrane surface. The base image generator generates a base image based on the image signals of the plurality of colors. The base image contains a first structure having a luminance value higher than a luminance value of a mucous membrane. The structure-extracted image generator generates a first structure-extracted image signal by subjecting a short-wavelength image signal containing a short-wavelength component out of the image signals of the plurality of colors to a first frequency component extracting process for extracting a first frequency component so as to extract a pixel of the first structure having a positive signal value. The display controlling image generator generates a display controlling image to be used for display control of the first structure based on the first structure-extracted image signal. The image compositor generates a display-controlled image in which display of the first structure is controlled by combining the display controlling image with the base image to combine the first structure of the display controlling image with the first structure of the base image.

The short-wavelength image signal is preferably a B image signal corresponding to a blue component. The B image signal is preferably a blue narrowband image signal. The image processing device further includes a narrow-band light source for emitting blue narrowband light. The blue narrowband image signal is preferably obtained by capturing an image of the mucous membrane surface illuminated with the blue narrowband light by the image signal generator. The image processing device further includes a spectral calculator for performing spectral calculation based on the image signals of the plurality of colors. The blue narrowband image signal is preferably obtained by the spectral calculation. The image processing device further includes a magnifying section for magnifying the mucous membrane surface. The short-wavelength image signal is preferably obtained in magnified observation using the magnifying section.

Preferably, the structure-extracted image generator subjects the short-wavelength image signal to the first frequency component extracting process so as to generate the first structure-extracted image signal in which the pixel of the first structure having a positive signal value is extracted and a second structure-extracted image signal in which a pixel of a second structure having a negative signal value is extracted. The display controlling image generator preferably generates a display controlling image to be used for display control of the first structure or the second structure based on the first and second structure-extracted image signals. Preferably, the image compositor generates a display-controlled image in which display of the first structure or the second structure is controlled by combining the display controlling image with the base image.

The display controlling image generator is preferably equivalent to a converter for outputting a display controlling image in which the pixel of the first structure or the second structure has a value corresponding to a display control degree in response to an input of the first and second structure-extracted image signals. The converter preferably includes a first converting section for outputting a display controlling image in which the pixel of the first structure has a positive value corresponding to an enhancement degree so as to enhance display of the first structure. The converter preferably includes a second converting section for outputting a display controlling image in which the pixel of the first structure has a negative value corresponding to a suppression degree so as to suppress display of the first structure. The converter preferably includes a third converting section for outputting a display controlling image in which the pixel of the second structure has a negative value corresponding to an enhancement degree so as to enhance display of the second structure. The converter preferably includes a fourth converting section for outputting a display controlling image in which the pixel of the second structure has a positive value corresponding to a suppression degree so as to suppress display of the second structure. The converter preferably includes a specific converting section for outputting a display controlling image in which the pixel of the first structure has a positive value, the pixel of the second structure has a negative value, and an absolute value of the pixel value of the first structure is different from an absolute value of the pixel value of the second structure, so as to enhance display of both of the first and second structures and make a difference between visual recognition of the first structure and visual recognition of the second structure.

Preferably, the image processing device further includes a distinguishing section and a gain processing section. The distinguishing section determines a pixel value of each of the first and second structure-extracted image signals. The gain processing section generates a display controlling image by performing a gain process corresponding to the display control degree of the first or second structure on the pixels of the first and second structure-extracted image signals each of which is determined to have a positive value or a negative value by the distinguishing section. The gain processing section preferably subjects the pixel determined to have a positive value and the pixel determined to have a negative value by the distinguishing section to a gain process for enhancement having a different enhancement degree corresponding to each of the pixels, so as to enhance display of both of the first and second structures and make a difference between the visual recognition of the first structure and the visual recognition of the second structure.

Preferably, the image processing device further includes a suppression processing section for subjecting the base image to a suppression process. In this case, the structure-extracted image generator subjects the short-wavelength image signal to the first frequency component extracting process, so as to generate the first structure-extracted image signal in which the pixel of the first structure having a positive signal value is extracted and a second structure-extracted image signal in which a pixel of a second structure having a negative signal value is extracted. Additionally, the display controlling image generator generates a display controlling image to be used to enhance display of a specific structure that is one of the first structure and the second structure based on the first and second structure-extracted image signals, and the image compositor generates a display-controlled image in which display of the specific structure that is one of the first structure and the second structure is enhanced and display of the other of the first structure and the second structure is suppressed by combining the display controlling image with the base image which has been subjected to the suppression process. Preferably, the first structure is a ductal structure and the second structure is capillary vessels.

A method for operating an endoscope system of the present invention includes an image signal generating step, a base image generating step, a structure-extracted image generating step, a display controlling image generating step, and an image compositing step. The image signal generating step generates image signals of a plurality of colors by capturing an image of a mucous membrane surface. The base image generating step generates a base image based on the image signals of the plurality of colors. The base image contains a first structure having a luminance value higher than a luminance value of a mucous membrane. The structure-extracted image generating step generates a first structure-extracted image signal by subjecting a short-wavelength image signal having a short-wavelength component out of the image signals of the plurality of colors to a first frequency component extracting process for extracting a first frequency component so as to extract a pixel of the first structure having a positive signal value. The display controlling image generating step generates a display controlling image to be used for display control of the first structure based on the first structure-extracted image signal. The image compositing step generates a display-controlled image in which display of the first structure is controlled by combining the display controlling image with the base image to combine the first structure of the display controlling image with the first structure of the base image.

According to the present invention, even in the case where the capillary vessels and the microstructure are separately diagnosed, it is possible to generate an endoscope image in which one of the capillary vessels and the microstructure does not impair the visual recognition of the other of the capillary vessels and the microstructure.

BRIEF DESCRIPTION OF DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 4 is a block diagram illustrating each component in a structure enhancement/suppression section;

FIG. 11 is a graph illustrating luminance distribution in a display-controlled image obtained by combining the display controlling image in FIG. 8C with a base image;

DESCRIPTION OF THE PREFERRED EMBODIMENTS

First Embodiment

Figure 1:
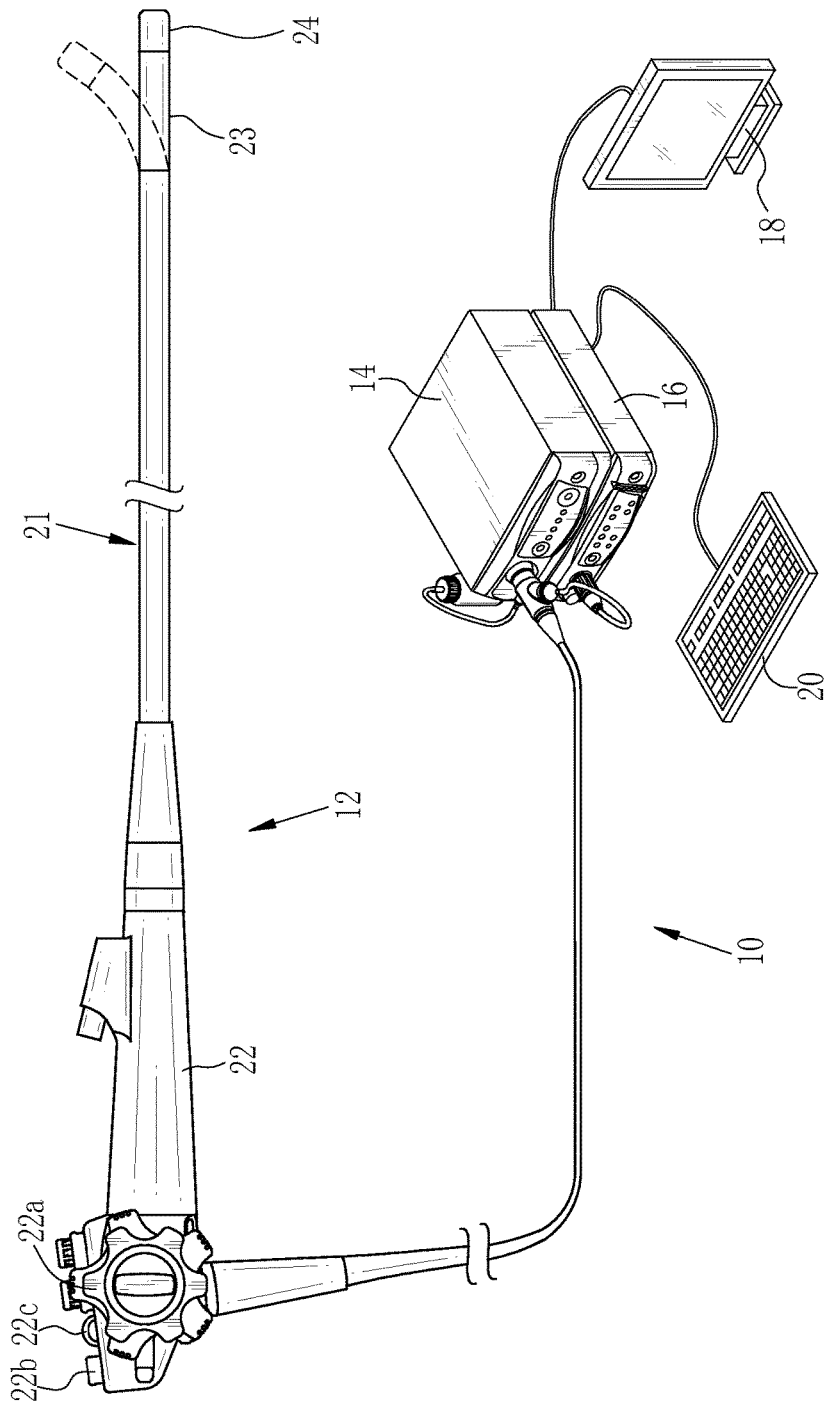
FIG. 1 is an external view of an endoscope system.

As shown in FIG. 1, an endoscope system 10 according to a first embodiment of the present invention includes an endoscope 12, a light source device 14, a processor device 16, a monitor 18, and a console 20. The endoscope 12 is optically connected to the light source device 14, and is electrically connected to the processor device 16. The endoscope 12 has an insert section 21, a handle section 22, a bending portion 23, and a distal portion 24. The insert section 21 is inserted into an observation object. The handle section 22 is provided in a proximal portion of the insert section 21. The bending portion 23 and the distal portion 24 are provided on a distal side of the insert section 21. The bending portion 23 is bent by operating an angle knob 22a of the handle section 22. The bending portion 23 is bent to direct the distal portion 24 to a desired direction.

In addition to the angle knob 22a, the handle section 22 is provided with a mode selection SW (switch) 22b and a zoom operation section 22c The mode selection SW 22b is used to switch between two modes, i.e., a normal observation mode and a special observation mode. White light is used in the normal observation mode. The normal observation mode is mostly for use in screening. Bluish special light is used in the special observation mode. The special observation mode is mostly for use in magnified observation. The zoom operation section 22c drives a zooming lens 47 (see FIG. 2), which is provided in the endoscope 12, to perform zoom operation for magnifying an observation object.

The processor device 16 is electrically connected to the monitor 18 and the console 20. The monitor 18 outputs and displays image information and the like. The console 20 serves as a UI (user interface) for accepting an input operation such as a function setting. Incidentally, external storage (not shown) may be connected to the processor device 16. The image information and the like are recorded in the external storage.

Figure 2:
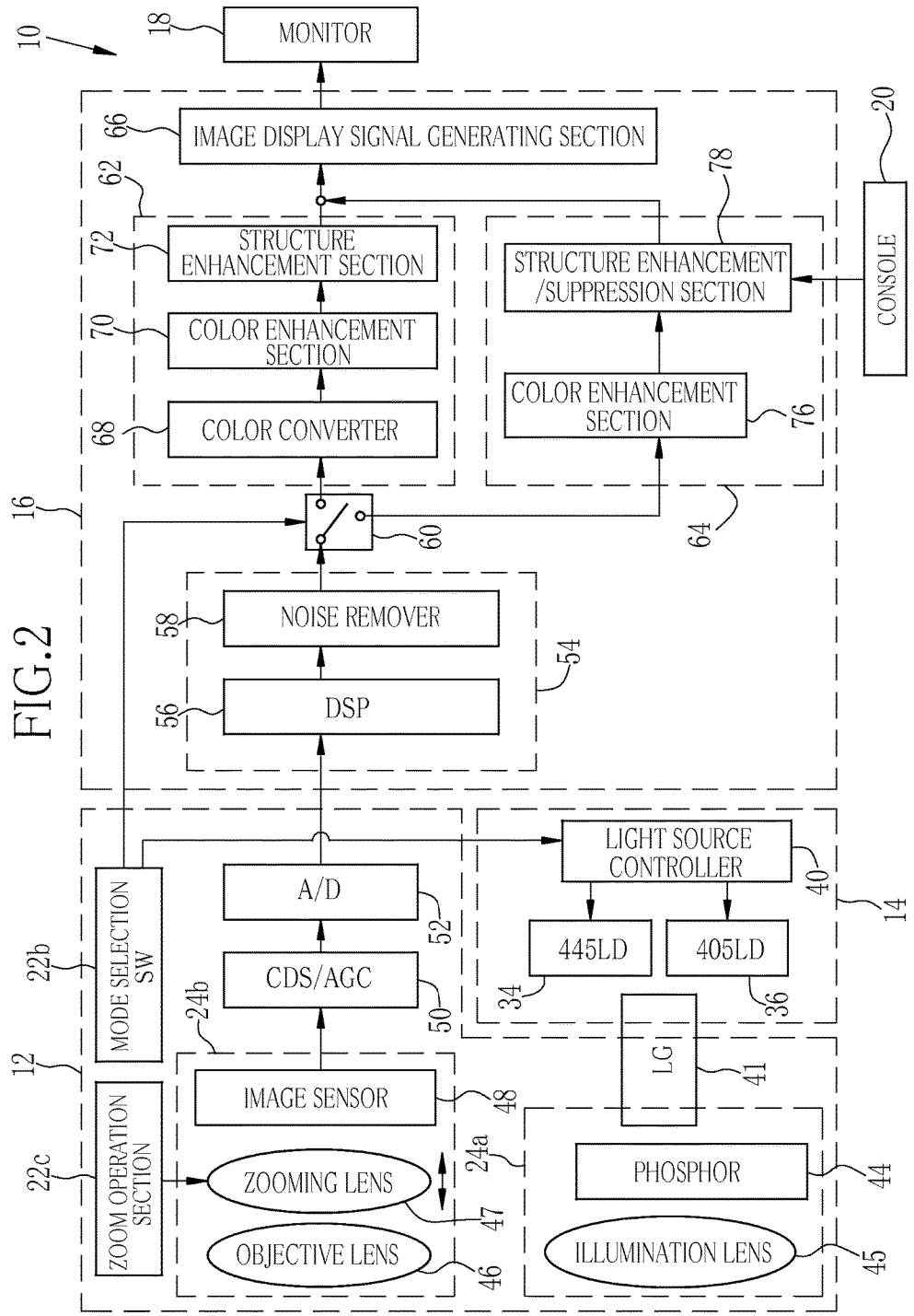
FIG. 2 is a block diagram illustrating each component in an endoscope system of a first embodiment.

As shown in FIG. 2, the light source device 14 includes a blue laser source (445LD) 34 and a blue-violet laser source (405LD) 36 as light sources. The blue laser source 34 emits blue laser beams with the center wavelength of 445 nm. The blue-violet laser source 36 emits blue-violet laser beams with the center wavelength of 405 nm. A light source controller 40 separately controls light emissions from semiconductor light emitting elements of the respective laser sources 34 and 36. A light quantity ratio between the emission beams from the blue laser source 34 and the emission beams from the blue-violet laser source 36 is changed as desired. In the normal observation mode, the light source controller 40 drives only the blue laser source 34. In contrast, in the special observation mode, the light source controller 40 drives both of the blue laser source 34 and the blue-violet laser source 36, such that the light quantity of the blue-violet laser beams is greater than that of the blue laser beams. Incidentally, any one of or both of the blue laser source 34 and the blue-violet laser source 36 constitutes/constitute a narrow-band light source of the present invention.

Note that, it is preferable that full width at half maximum of the blue laser beams or the blue-violet laser beams is in the order of ±10 nm. In the normal observation mode, the blue-violet laser source 36 also may be turned on. However, in this case, emission intensity of the blue-violet laser source 36 is preferably suppressed to a low level. The blue laser source 34 and the blue-violet laser source 36 may be broad-area InGaN laser diodes, InGaNAs laser diodes, or GaNAs laser diodes. A light emitter such as a light emitting diode may be used as the above-described light source.

The laser beams emitted from the laser source 34 or 36 are incident on a light guide (LG) 41 through optical members such as a condenser lens, an optical fiber, and a combiner (all not shown). The light guide 41 is incorporated in the endoscope 12 and a universal cord which connects the light source device 14 and the endoscope 12. The blue laser beams with the center wavelength of 445 nm or the blue-violet laser beams with the center wavelength of 405 nm propagate through the light guide 41 to the distal portion 24 of the endoscope 12. Incidentally, a multi-mode fiber may be used as the light guide 41. For example, a small-diameter fiber cable with a core diameter of 105 μm and a clad diameter of 125 μm may be used. The total diameter φ of the fiber cable, including a protection layer as an outer sheath, is in the range of 0.3 to 0.5 mm.

The distal portion 24 of the endoscope 12 has an illuminating optical system 24a and an imaging system 24b. The illuminating optical system 24a is provided with a phosphor 44 and an illumination lens 45. The blue laser beams with the center wavelength of 445 nm or the blue-violet laser beams with the center wavelength of 405 nm are incident on the phosphor 44 from the light guide 41. Fluorescence is emitted from the phosphor 44 upon application of the blue laser beams to the phosphor 44. Part of the blue laser beams passes through the phosphor 44. The blue-violet laser beams passes through the phosphor 44 without exciting the phosphor 44. The light from the phosphor 44 is applied to the inside of the observation object through the illumination lens 45.

Figure 3A:
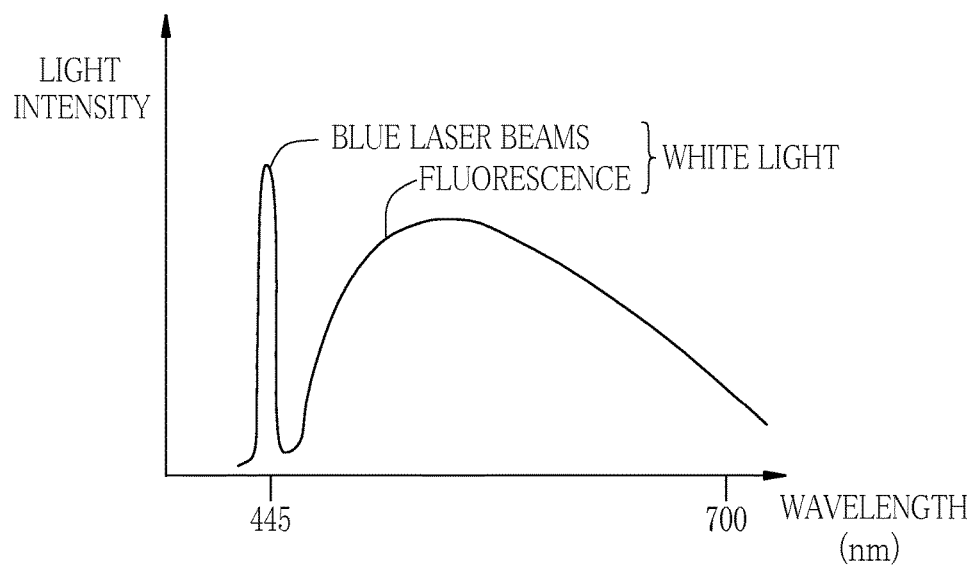
FIG. 3A is a graph illustrating emission spectra of white light.
Figure 3B:
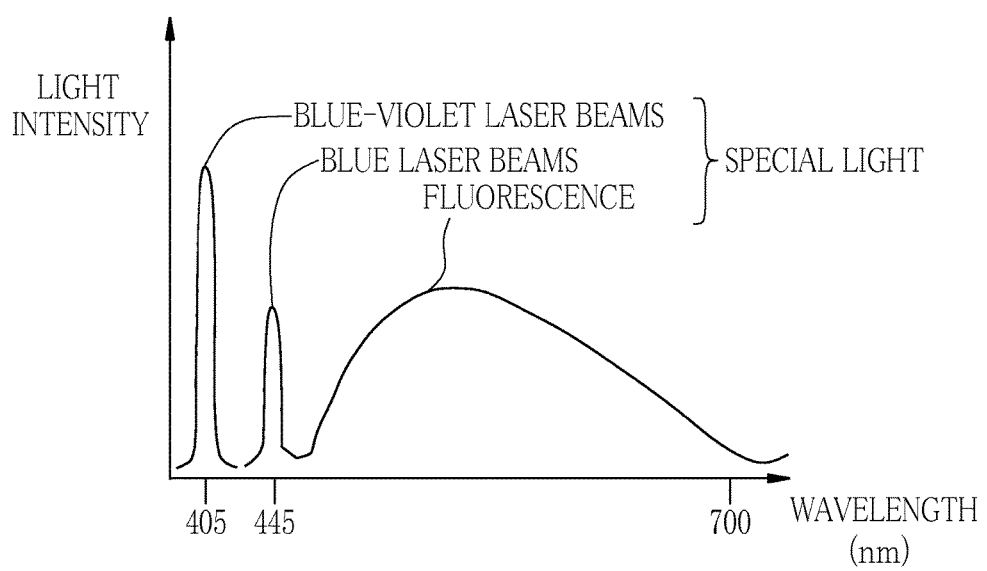
FIG. 3B is a graph illustrating emission spectra of special light.

In the normal observation mode, only the blue laser beams are incident on the phosphor 44. Thereby, as shown in FIG. 3A, white light generated by mixing the blue laser beams and the fluorescence is applied to the inside of the observation object. The fluorescence is emitted from the phosphor 44 which is excited by the blue laser beams. In contrast, in the special observation mode, both of the blue-violet laser beams and the blue laser beams are incident on the phosphor 44. Hence, as shown in FIG. 3B, the special light is applied to the inside of the observation object. The special light is generated by mixing the blue-violet laser beams, the blue laser beams, and the fluorescence emitted from the phosphor 44 excited by the blue laser beams. In the special observation mode, the light quantity of the blue-violet laser beams is greater than that of the blue laser beams. Hence, the special light contains a high proportion of blue components, and the wavelength range of the special light covers substantially the entire visible light region.

Note that, it is preferable to use the phosphor 44 composed of two or more fluorescent substances (for example, YAG fluorescent substances or BAM(BaMgAl$_{10}$O$_{17}$)) which absorb part of the blue laser beams to emit light of green to yellow. As described in this embodiment, with the use of the semiconductor light emitting element as the excitation light source for the phosphor 44, the white light with high intensity is emitted with high light emission efficiency, and the intensity of the white light is adjusted easily. Additionally, fluctuations in color temperature and chromaticity of the white light are suppressed to a small extent.

As shown in FIG. 2, the imaging system 24b of the endoscope 12 has an objective lens 46, the zooming lens 47, and an image sensor 48. Light reflected from the observation object is incident on the image sensor 48 through the objective lens 46 and the zooming lens 47. Thereby, a reflection image of the observation object is formed on the image sensor 48. The zooming lens 47 is moved between a telephoto end and a wide-angle end by operating the zoom operation section 22c. The reflection image of the observation object is reduced when the zooming lens 47 is moved to the wide-angle end side. The reflection image of the observation object is magnified when the zooming lens 47 is moved to the telephoto end side.

The image sensor 48 is a color image sensor. The image sensor 48 captures a reflection image of the observation object and outputs image signals. Incidentally, the image sensor 48 is preferably a CCD (Charge Coupled Device) image sensor, a CMOS (Complementary Metal-Oxide Semiconductor) image sensor, or the like. The image sensor used in the present invention may be an RGB color image sensor or a complementary color image sensor. The RGB image sensor has an RGB filter on its imaging surface to obtain image signals of three colors, R (red), G (green), and B (blue) An imaging surface of the complementary color image sensor is provided with a complementary color filter of C (cyan), M (magenta), Y (yellow), and G (green). In the case where the complementary color image sensor is used, the image signals which represent luminance values of the three colors (RGB) respectively are obtained by color conversion of the image signals of four colors (CMYG). In this case, it is necessary that one of the endoscope 12, the light source device 14, and the processor device 16 includes a color converter for converting the image signals of four colors (CMYG) into the image signals of three colors (RGB).

The image signal outputted from the image sensor 48 is transmitted to a CDS/AGC circuit 50. The CDS/AGC circuit 50 performs correlated double sampling (CDS) and automatic gain control (AGC) on the image signal as an analog signal. An A/D converter 52 converts the image signal which has passed through the CDS/AGC circuit 50 into a digital image signal. The A/D-converted digital image signal is inputted to the processor device 16.

The processor device 16 includes a receiver 54, an image processor selector 60, a normal image processor 62, a special image processor 64, and an image display signal generating section 66. The receiver 54 receives the digital image signal from the endoscope 12. The receiver 54 includes a DSP (Digital Signal Processor) 56 and a noise remover 58. The DSP 56 performs gamma correction and a color correction process on the digital image signal. The noise remover 58 performs a noise removal process (for example, moving average method, median filter method, or the like) on the digital image signal which has been subjected to the gamma correction and the like in the DSP 56.

Thereby, noise is removed from the digital image signal. The digital image signal from which noise has been removed is transmitted to the image processor selector 60.

In the case where the endoscope system 10 is set to the normal observation mode by the use of the mode selection SW 22b, the image processor selector 60 transmits the digital image signal to the normal image processor 62. In the case where the endoscope system 10 is set to the special observation mode, the image processor selector 60 transmits the digital image signal to the special image processor 64. Note that, in the present invention, for distinction, the digital image signal before being subjected to the image processing by the normal image processor 62 or the special image processor 64 is referred to as an image signal, and the digital image signal after being subjected to the image processing is referred to as image data.

The normal image processor 62 has a color converter 68, a color enhancement section 70, and a structure enhancement section 72. The color converter 68 assigns the inputted digital image signals of three channels (R, G, and B) to R image data, G image data, and B image data, respectively. The RGB image data is further subjected to color conversion processes such as a matrix process of 3×3, a tone reversal process, and a three-dimensional LUT process. Thereby, the RGB image data is converted into color-converted RGB image data.

The color enhancement section 70 performs various color enhancement processes on the color-converted RGB image data. The structure enhancement section 72 performs structure enhancement processes for enhancing sharpness, edges, and the like on the color-enhanced RGB image data. The RGB image data which has been subjected to the structure enhancement processes in the structure enhancement section 72 is inputted as a normal image from the normal image processor 62 to the image display signal generating section 66.

The special image processor 64 has a color enhancement section 76 and a structure enhancement/suppression section 78. The color enhancement section 76 performs various color enhancement processes on the inputted digital image signals of three channels (R, G, and B) so as to generate a color-enhanced RGB image signal. The structure enhancement/suppression section 78 subjects the color-enhanced RGB image signal to structure enhancement/suppression processes for enhancing/suppressing the display of a ductal structure S or blood vessels so as to generate a display-controlled image. The display-controlled image which has been subjected to the structure enhancement/suppression processes in the structure enhancement/suppression section 78 is inputted as a special image from the special image processor 64 to the image display signal generating section 66.

As shown in FIG. 4, the structure enhancement/suppression section 78 includes a base image generator 80, a frequency filtering section 81, a display controlling image generator 82, and an image composition section 83. Out of the color-enhanced RGB image signal, the base image generator 80 assigns the G image signal to the R image data, and assigns the B image signal to the G image data and the B image data. Thus, the RGB image data forms a base image. In the base image, although the B image signal is assigned to the B image data, not the G image signal but the B image signal is assigned to the G image data, and not the R image signal but the G image signal is assigned to the R image data. Hence, the base image is displayed in pseudo colors. Note that, the base image generator 80 may assign the R, G, and B image signals to the RGB image data to generate a base image based on white light, instead of the pseudo color image, in a manner similar to the color converter 68.

The frequency filtering section 81 performs a frequency filtering process on the color-enhanced B image signal to extract a frequency band component corresponding to the ductal structure S and the capillary vessels V in the surface layer of a mucous membrane. Here, the ductal structure S extracted in the frequency filtering process is a marginal portion which seems to be edged with white. Incidentally, not only the marginal portion but also a duct orifice is included in a duct. Hence, a structure-extracted image signal 85, in which the ductal structure S and the capillary vessels V are extracted, is obtained. The reason why the B image signal is subjected to the frequency filtering process is that the B image signal corresponds to the blue components of the light such as the blue-violet laser beams and the blue laser beams which can apply a structure-enhancing effect on the ductal structure S and the capillary vessels V.

Figure 5A:
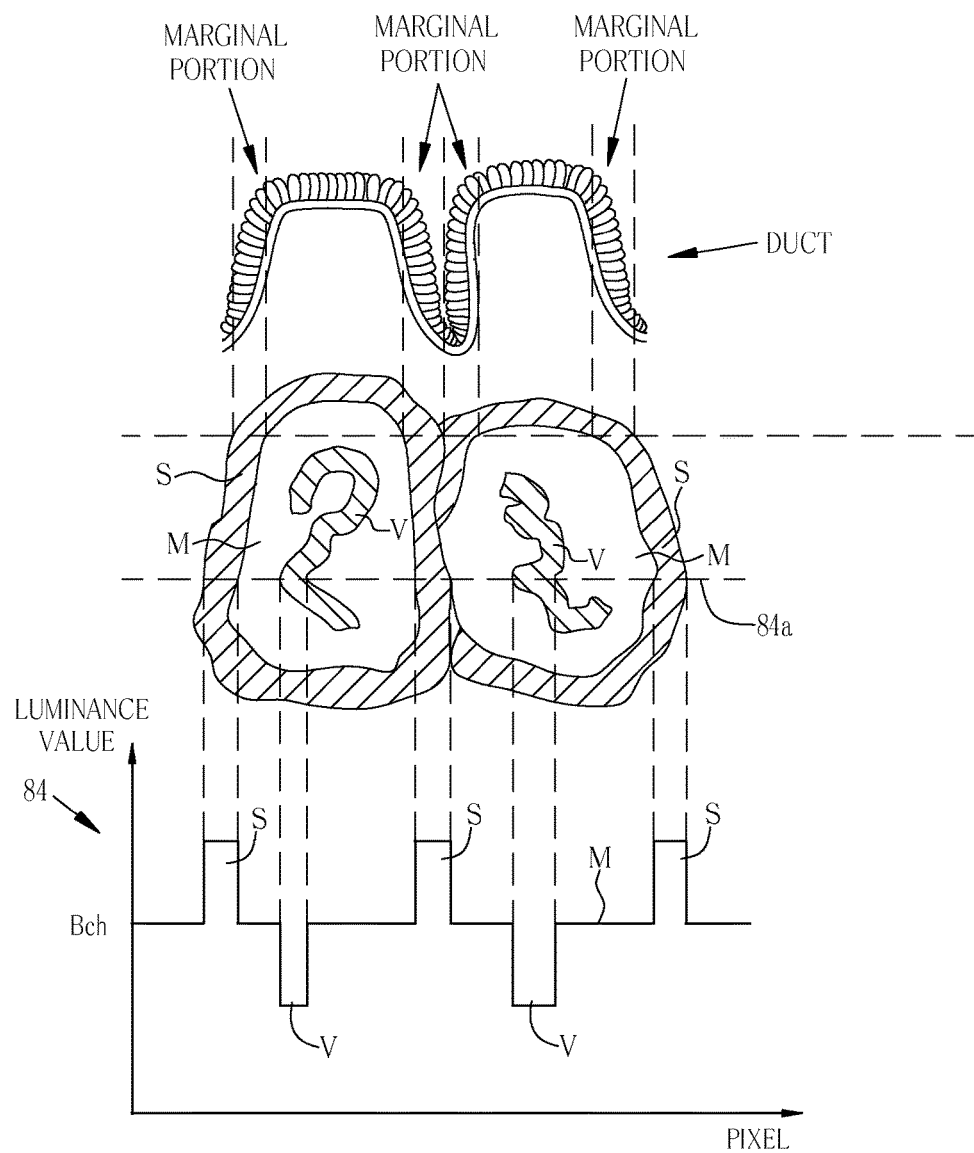
FIG. 5(A) is a graph illustrating distribution of luminance values in a predefined pixel line in a B image signal (Bch)
Figure 5B:
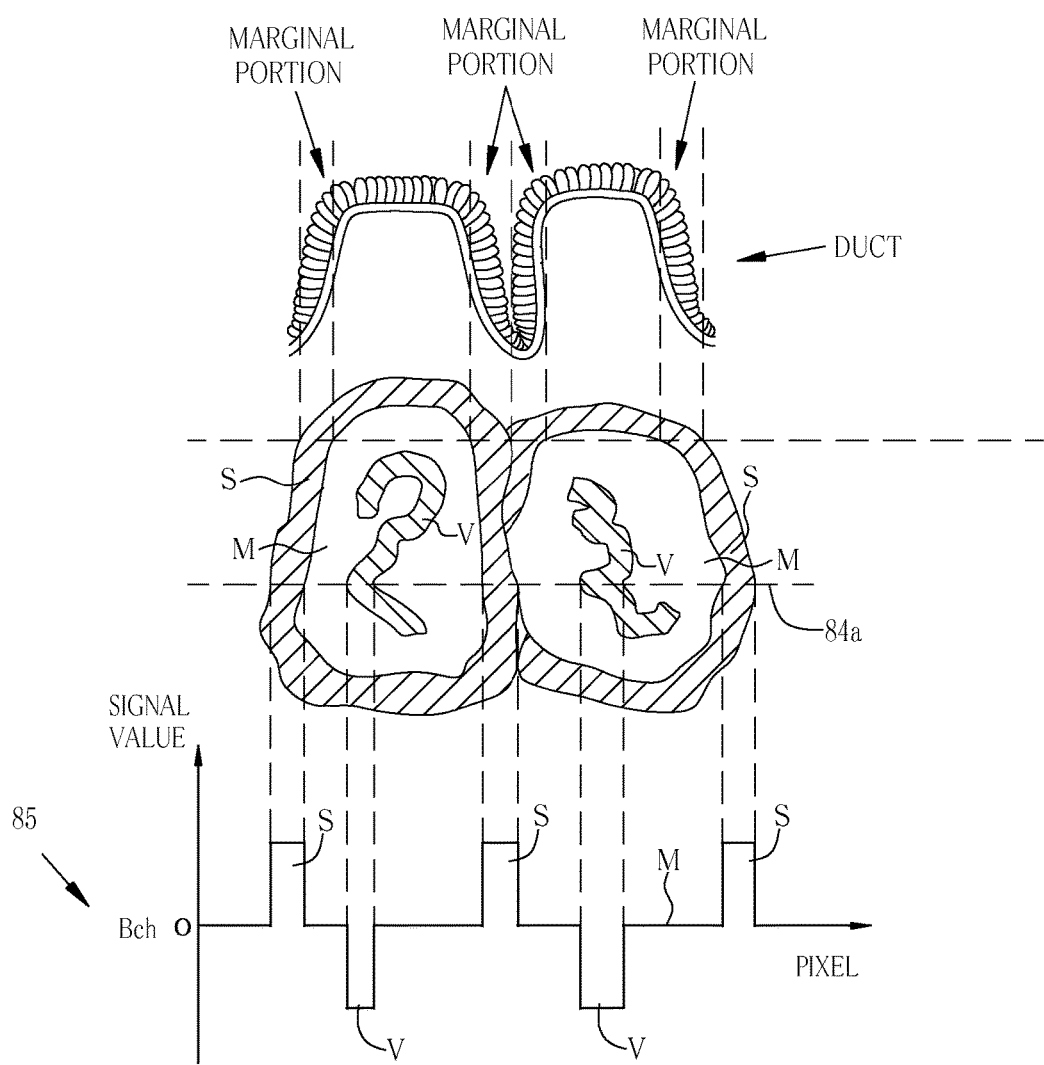
FIG. 5(B) is a graph illustrating distribution of signal values in a structure-extracted image signal after a frequency filtering process.

Note that, as shown in FIG. 5(A), the ductal structure S is reflected diffusely due to the blue components of the light such as the blue-violet laser beams and the blue laser beams, and therefore the ductal structure S is displayed brighter than the mucous membrane M in a B image signal 84. Unlike the blue narrowband light separated from broadband light such as xenon light, the blue-violet laser beams and the blue laser beams are highly rectilinear, so that the laser beams reach the bottoms of pits in the ductal structure S. Thereby, the ductal structure S is displayed brighter than that illuminated by the blue narrowband light. In contrast, the capillary vessels V well-absorb the blue components of the light such as the blue-violet laser beams and the blue laser beams, in which an extinction coefficient of hemoglobin is high, out of the special light. Hence, the capillary vessels V are displayed darker than the mucous membrane M in the B image signal 84. Thus, as shown in FIG. 5(B), in a structure-extracted image signal 85 which has been subjected to the frequency filtering process, the pixel corresponding to the ductal structure S has a "positive" signal value (i.e., a signal value on a rising edge), and the pixel corresponding to the capillary vessels V has a "negative" signal value (i.e., a signal value on a falling edge). There is substantially no change in luminance value of the mucous membrane M in the structure-extracted image signal 85, so that a signal value of the pixel corresponding to the mucous membrane M is approximately "0". Note that, in FIG. 5, the B image signal 84 represents a luminance value of each pixel on a line 84a, and the structure-extracted image signal 85 represents a signal value of each pixel on the line 84a. (The same holds true for FIGS. 11 to 13.) Here, the signal value includes "0", a positive value, and a negative value. The luminance value includes "0" and a positive value.

The display controlling image generator 82 generates a display controlling image to be used for enhancing, suppressing, or keeping a display state of the ductal structure S or the capillary vessels V from the structure-extracted image signal 85. The display controlling image generator 82 includes a converter 86 to which the structure-extracted image signal 85 is inputted and from which the display controlling image is outputted, and a structure enhancement/suppression setting section 87 for setting enhancement/suppression conditions and controlling the converter 86 in accordance with the set enhancement/suppression conditions (see FIG. 4).

Figure 6:
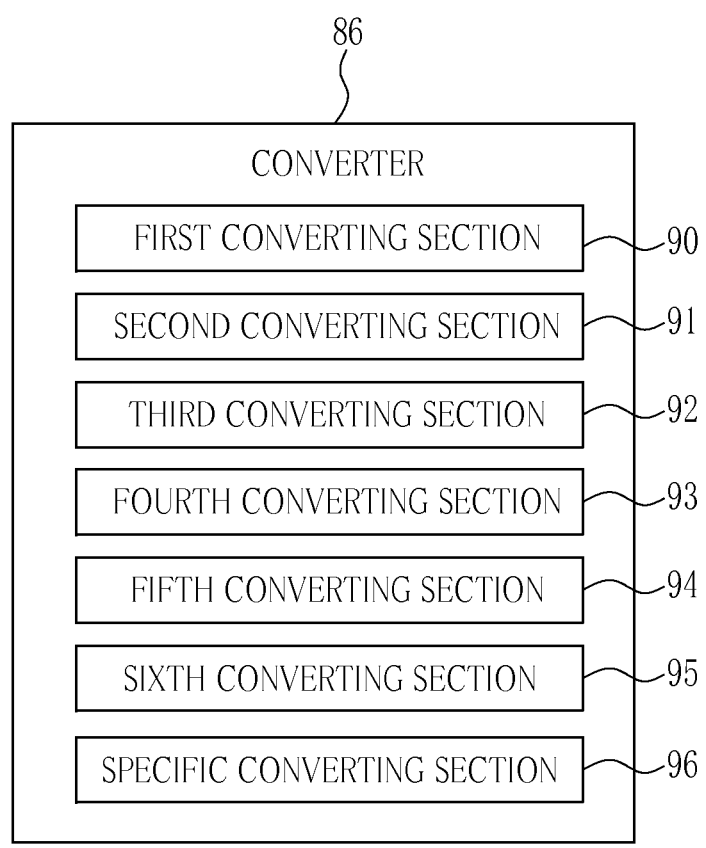
FIG. 6 is a block diagram illustrating each component of a converter.

As shown in FIG. 6, the converter 86 consists of a first converting section 90, a second converting section 91, a third converting section 92, a fourth converting section 93, a fifth converting section 94, a sixth converting section 95, and a specific converting section 96. In response to an input of the structure-extracted image signal 85, the converter 86 outputs the display controlling image signal having a value corresponding to the display control degree such as the enhancement degree and the suppression degree of the display of the ductal structure S or the capillary vessels V. The first converting section 90 is used to enhance the display of the ductal structure S, and outputs a value corresponding to an input and output relationship 90a shown in FIG. 7 in response to an input of the structure-extracted image signal 85. The input and output relationship 90a is defined by a positive slope so as to output a positive value in response to an input of the structure-extracted image signal 85 with a positive value. The outputted positive value is added to the ductal structure S in the base image, and thereby the ductal structure S, which is brighter than the mucous membrane M, becomes further brighter, and therefore a contrast between the mucous membrane M and the ductal structure S is increased. As a result, an enhancing effect on the ductal structure can be obtained. Incidentally, in the first converting section 90, input and output relationships corresponding to four enhancement degrees, i.e., a first enhancement degree E1, a second enhancement degree E2, a third enhancement degree E3, and a fourth enhancement degree E4 are defined. As the enhancement degree becomes larger, the slope of the input and output relationship corresponding to the enhancement degree becomes larger.

Figure 7:
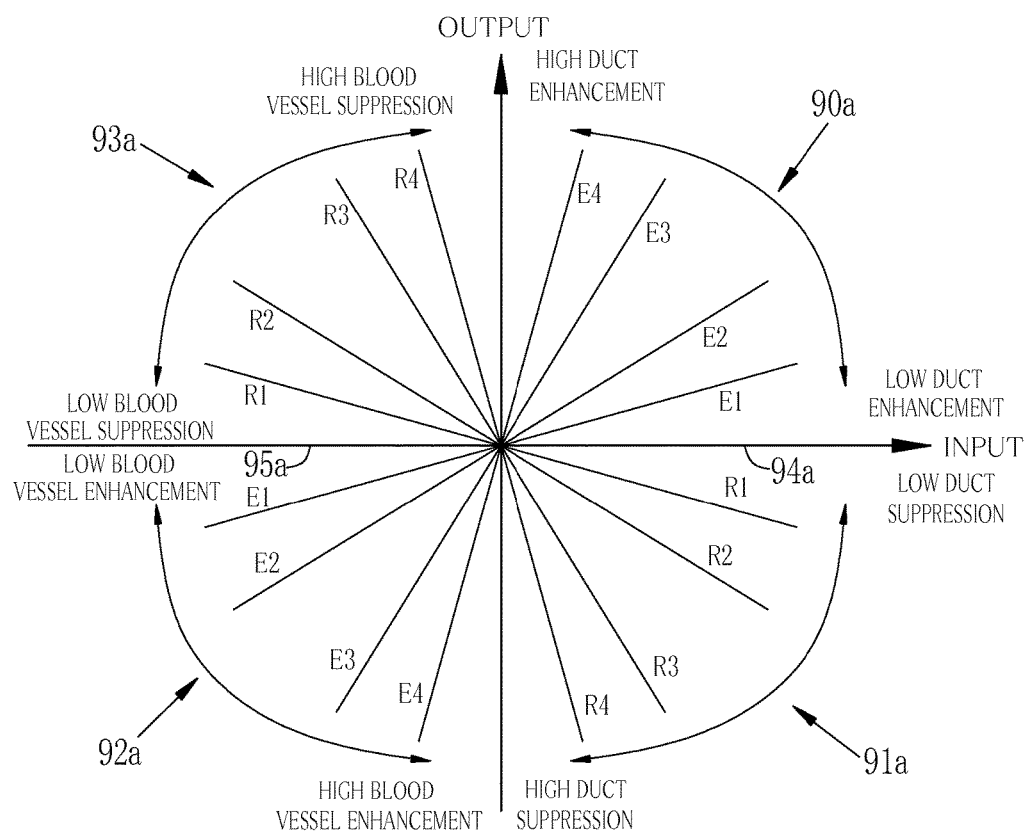
FIG. 7 is an explanatory view illustrating an input and output relationship in each converting section of the converter.

The second converting section 91 is used to suppress the display of the ductal structure S, and outputs a value corresponding to an input and output relationship 91a shown in FIG. 7 in response to an input of the structure-extracted image signal 85. The input and output relationship 91a is defined by a negative slope so as to output a negative value in response to an input of the structure-extracted image signal 85 with a positive value. The outputted negative value is added to the ductal structure S in the base image, and thereby the brightness of the ductal structure S becomes closer to that of the mucous membrane M, and therefore a contrast between the mucous membrane M and the ductal structure S is decreased. As a result, a suppressing effect on the ductal structure can be obtained. Incidentally, in the second converting section 91, input and output relationships corresponding to four suppression degrees, i.e., a first suppression degree R1, a second suppression degree R2, a third suppression degree R3, and a fourth suppression degree R4 are defined. As the suppression degree becomes larger, the slope of the input and output relationship corresponding to the suppression degree becomes larger.

The third converting section 92 is used to enhance the display of the capillary vessels V, and outputs a value corresponding to an input and output relationship 92a shown in FIG. 7 in response to an input of the structure-extracted image signal 85. The input and output relationship 92a is defined by a positive slope so as to output a negative value in response to an input of the structure-extracted image signal 85 with a negative value. The outputted negative value is added to the capillary vessels V in the base image, and thereby the capillary vessels V, which are darker than the mucous membrane M, become further darker, and therefore a contrast between the mucous membrane M and the capillary vessels V is increased. As a result, an enhancing effect on the capillary vessels can be obtained. Incidentally, in the third converting section 92, input and output relationships corresponding four enhancement degrees, i.e., a first enhancement degree E1, a second enhancement degree E2, a third enhancement degree E3, and a fourth enhancement degree E4 are defined. As the enhancement degree becomes larger, the slope of the input and output relationship corresponding to the enhancement degree becomes larger.

The fourth converting section 93 is used to suppress the display of the capillary vessels V, and outputs a value corresponding to an input and output relationship 93a shown in FIG. 7 in response to an input of the structure-extracted image signal 85. The input and output relationship 93a is defined by a negative slope so as to output a positive value in response to an input of the structure-extracted image signal 85 with a negative value. The outputted positive value is added to the capillary vessels V in the base image, and thereby the brightness of the capillary vessels V becomes closer to that of the mucous membrane M, and therefore a contrast between the mucous membrane M and the capillary vessels V is decreased. As a result, a suppressing effect on the capillary vessels can be obtained. Incidentally, in the fourth converting section 93, input and output relationships corresponding four suppression degrees, i.e., a first suppression degree R1, a second suppression degree R2, a third suppression degree R3, and a fourth suppression degree R4 are defined. As the suppression degree becomes larger, the slope of the input and output relationship corresponding to the suppression degree becomes larger.

The fifth converting section 94 is used to keep the brightness of the ductal structure S, and outputs a value of "0" in accordance with an input and output relationship 94a shown in FIG. 7 in response to an input of the structure-extracted image signal 85 with a positive value. The value of "0" is added to the ductal structure S in the base image, and thereby brightness of the ductal structure S is kept. The sixth converting section 95 is used to keep the brightness of the capillary vessels V, and outputs a value of "0" in accordance with an input and output relationship 95a shown in FIG. 7 in response to an input of the structure-extracted image signal 85 with a negative value. The value of "0" is added to the capillary vessels V in the base image, and thereby brightness of the capillary vessels V is kept.

Figure 8A:
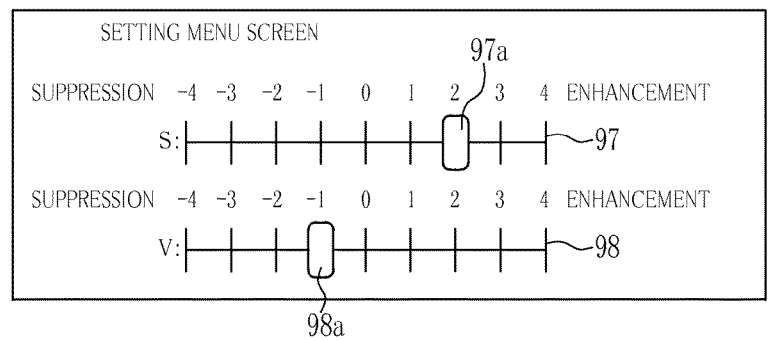
FIG. 8A is an image of a setting menu screen for enhancement of display of a ductal structure and suppression of display of capillary vessels.
Figure 9A:
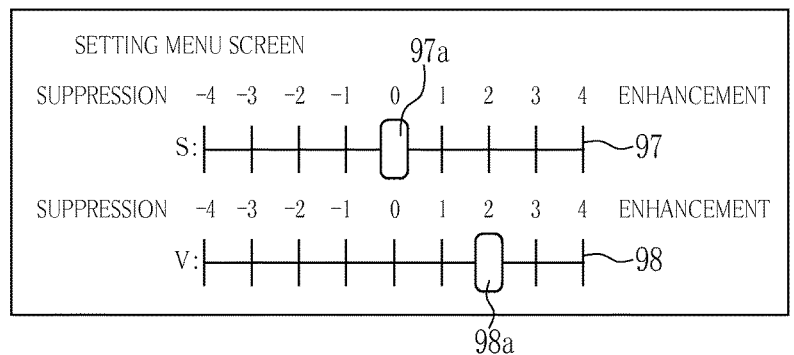
FIG. 9A is an image of a setting menu screen for enhancement of display of only the capillary vessels.
Figure 10A:
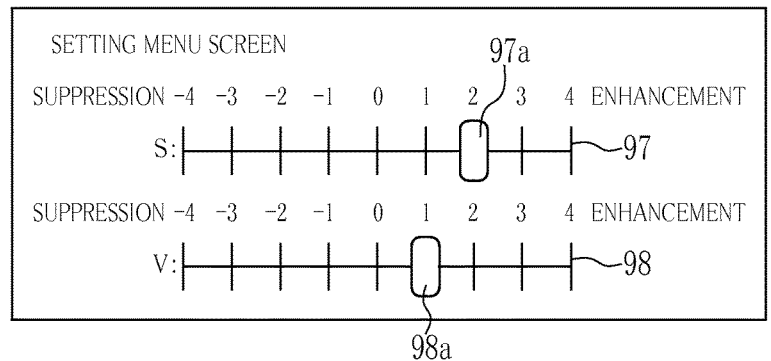
FIG. 10A is an image of a setting menu screen for enhancement of display of the ductal structure and enhancement of display of the capillary vessels.

The structure enhancement/suppression setting section 87 controls the converter 86 in accordance with the enhancement/suppression conditions inputted by the console 20. The setting of the enhancement/suppression conditions is performed while a setting menu screen as shown in FIGS. 8A, 9A, and 10A is displayed on the monitor 18. A "S" slide bar 97 for setting the enhancement/suppression conditions of the ductal structure S and a "V" slide bar 98 for setting the enhancement/suppression conditions of the capillary vessels V are displayed on the setting menu screen.

In the case where a slider 97a is set to "0" at the center on the "S" slide bar 97, the conditions for keeping the brightness of the ductal structure S are set. In this case, the structure-extracted image signal 85 is inputted to the fifth converting section 94. In the case where the slider 97a is slid to the right side representing the enhancement of the display on the "S" slide bar 97, the conditions for enhancing the display of the ductal structure S are set. In this case, the structure-extracted image signal 85 is inputted to the first converting section 90. In the case where the slider 97a is slid to the left side representing the suppression of the display on the "S" slide bar 97, the conditions for suppressing the display of the ductal structure S are set. In this case, the structure-extracted image signal 85 is inputted to the second converting section 91.

Further, scales "1" to "4" and "−1" to "−4" on the "S" slide bar 97 respectively correspond to the first to fourth enhancement degrees E1 to E4 and the first to fourth suppression degrees R1 to R4 defined by the converter 86.

Accordingly, upon setting of the slider 97a to a predetermined scale, the enhancement degree or the suppression degree is set so as to correspond to the set scale by the converter 86. Incidentally, in the same manner as that of the "S" slide bar 97, the slider 98a of the "V" slide bar is used to set the conditions for the enhancement and suppression of the capillary vessels V.

Figure 8B:
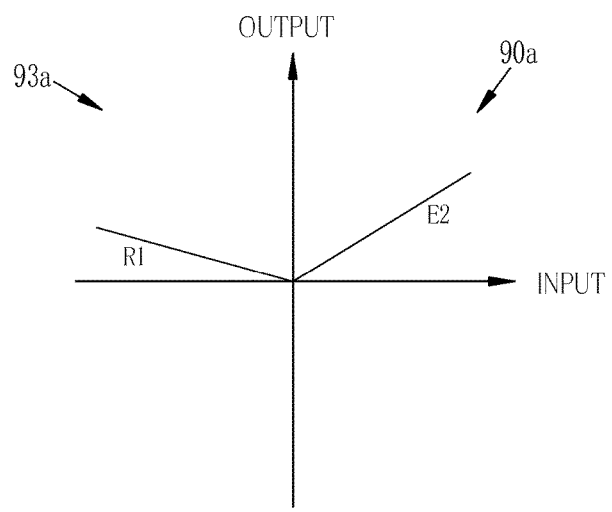
FIG. 8B is an explanatory view illustrating an input and output relationship in the converter at the time of performing enhancement of display of the ductal structure and suppression of display of the capillary vessels.
Figure 8C:
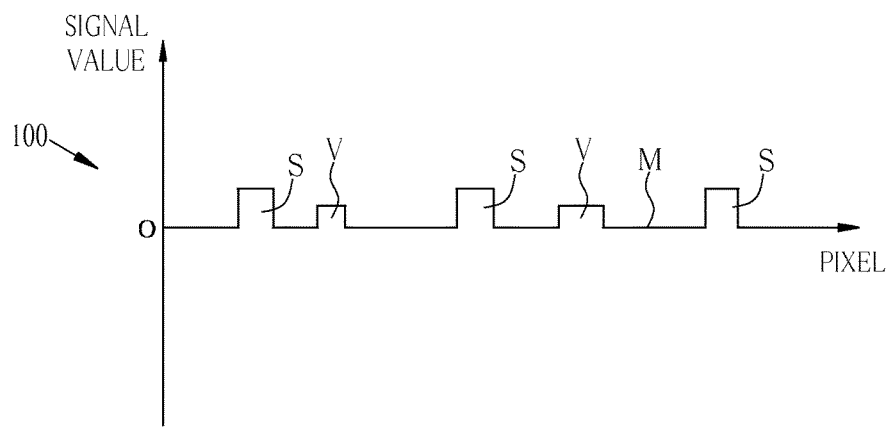
FIG. 8C is a graph illustrating distribution of signal values in a display controlling image to be used for enhancement of display of the ductal structure and suppression of display of the capillary vessels.

For example, in the case where the slider 97a is set to "+2" on the "S" slide bar 97 and the slider 98a is set to "−1" on the "V" slide bar 98 as shown in FIG. 8A, the slope of the input and output relationship 90a is set to the second enhancement degree E2 in the first converting section 90, and the slope of the input and output relationship 93a is set to the first suppression degree R1 in the fourth converting section 93, as shown in FIG. 8B. Then, the structure-extracted image signal 85 is inputted to the first converting section 90 and the fourth converting section 93, so as to output a display controlling image 100 in which both the signal value of the pixel of the ductal structure S and the signal value of the pixel of the capillary vessels V are positive values, as shown in FIG. 8C. The display controlling image 100 is used to perform diagnoses based on observation of the ductal structure S.

Figure 9B:
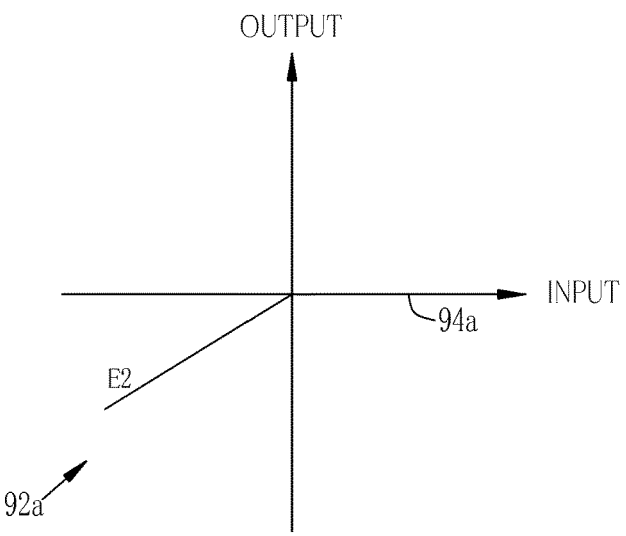
FIG. 9B is an explanatory view illustrating an input and output relationship in the converter at the time of performing enhancement of display of only the capillary vessels.
Figure 9C:
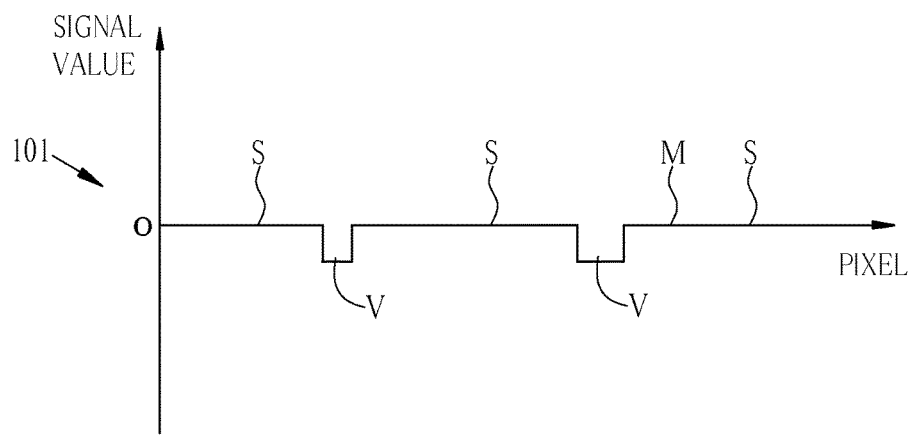
FIG. 9C is a graph illustrating distribution of signal values in a display controlling image to be used for enhancement of display of only the capillary vessels.

Further, in the case where the slider 97a is set to "0" on the "S" slide bar 97 and the slider 98a is set to "+2" on the "V" slide bar 98 as shown in FIG. 9A, the slope of the input and output relationship 92a is set to the second enhancement degree E2 in the third converting section 92 as shown in FIG. 9B. Then, the structure-extracted image signal 85 is inputted to the fifth converting section 94 and the third converting section 92, so as to output a display controlling image 101 in which the signal value of the pixel of the ductal structure S is "0" and the signal value of the pixel of the capillary vessels V is a negative value, as shown in FIG. 9C. The display controlling image 101 is used to perform diagnoses based on observation of the capillary vessels V.

Figure 10B:
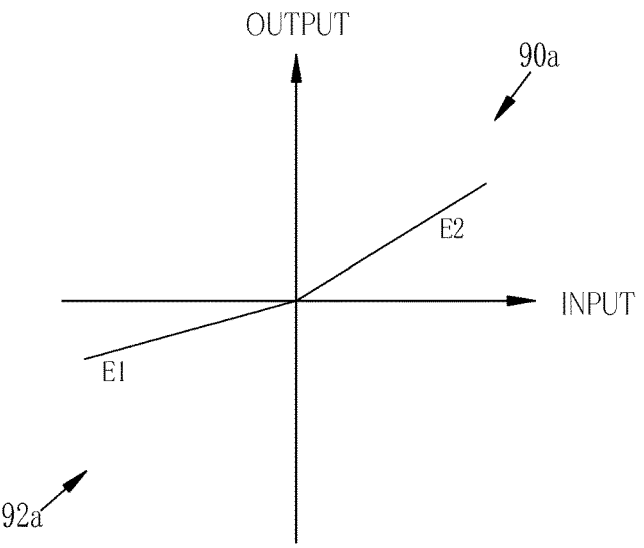
FIG. 10B is an explanatory view illustrating an input and output relationship in the converter at the time of performing enhancement of display of the ductal structure and enhancement of display of the capillary vessels.
Figure 10C:
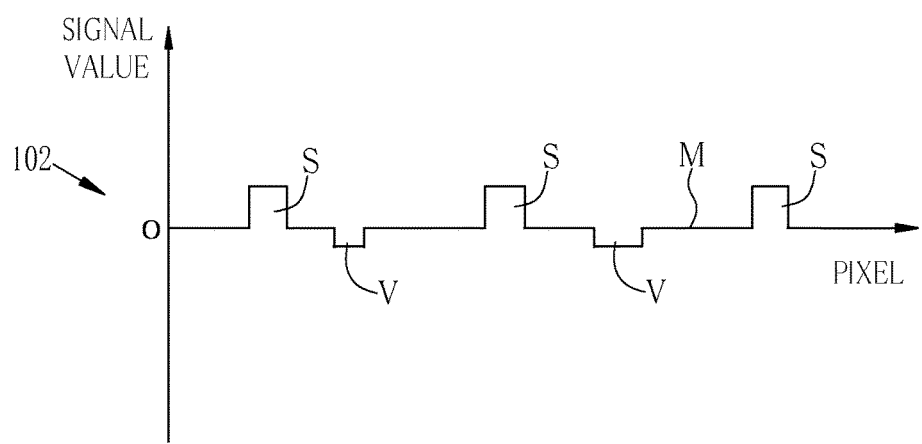
FIG. 10C is a graph illustrating distribution of signal values in a display controlling image to be used for enhancement of display of the ductal structure and enhancement of display of the capillary vessels.

Furthermore, in the case where the slider 97a is set to "+2" on the "S" slide bar 97 and the slider 98a is set to "+1" on the "V" slide bar 98 as shown in FIG. 10A, the slope of the input and output relationship 90a is set to the second enhancement degree E2 in the first converting section 90, and the slope of the input and output relationship 92a is set to the first enhancement degree E1 in the third converting section 92 as shown in FIG. 10B. Then, the structure-extracted image signal 85 is inputted to a specific converting section 96 having a conversion function of both of the first converting section 90 and the third converting section 92, so as to output a display controlling image 102 in which the signal value of the pixel of the ductal structure S is a positive value and the signal value of the pixel of the capillary vessels V is a negative value, as shown in FIG. 10C.

In the display controlling image 102, since the enhancement degree of the ductal structure S is higher than that of the capillary vessels V, an absolute value of the pixel value of the ductal structure S is larger than that of the capillary vessels V. Therefore, the display controlling image 102 is used to enhance the display of both of the ductal structure S and the capillary vessels V, and concurrently, to enhance the visual recognition of the ductal structure S in comparison with that of the capillary vessels V.

The image composition section 83 combines the display controlling image with the base image. Thereby, a display-controlled image, in which the display of the ductal structure S or the capillary vessels V is enhanced or suppressed, is generated. Although the image composition section 83 adds pixel values of the display controlling image 102 to the respective pixel values (Bch) of the B image data of the base image, the pixel values of the display controlling image 102 may be added to the respective pixels of the G image data or the R image data.

For example, in the case where the display controlling image 100, in which both the signal value of the pixel of the ductal structure S and the signal value of the pixel of the capillary vessels V are positive values as shown in FIG. 8C, is combined with Bch (respective pixels of the B image data) of a base image 105, a display-controlled image 110, in which the contrast between the ductal structure S and the surrounding mucous membrane M is increased and the contrast between the capillary vessels V and the surrounding mucous membrane M is decreased as shown in FIG. 11, is obtained. Incidentally, dotted lines denote luminance values before the image composition.

Figure 12:
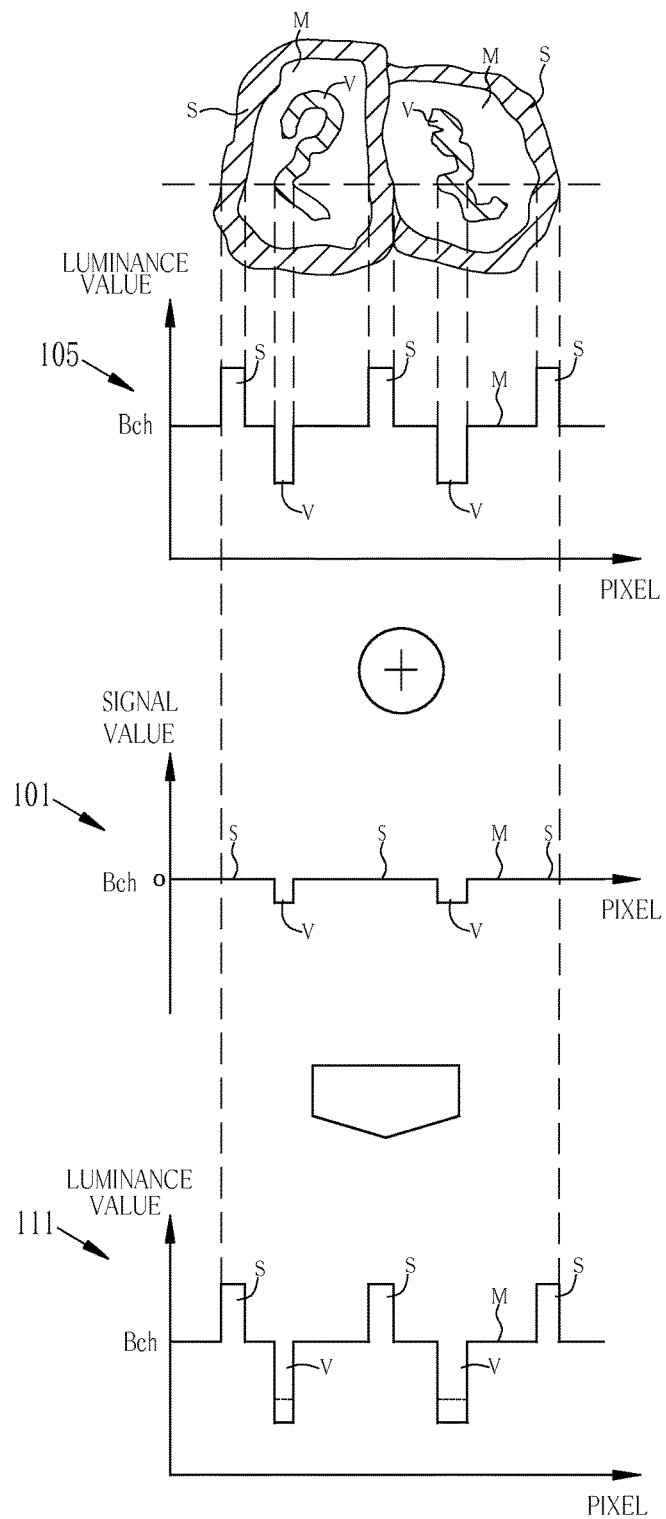
FIG. 12 is a graph illustrating luminance distribution in a display-controlled image obtained by combining the display controlling image in FIG. 9C with the base image.
Figure 13:
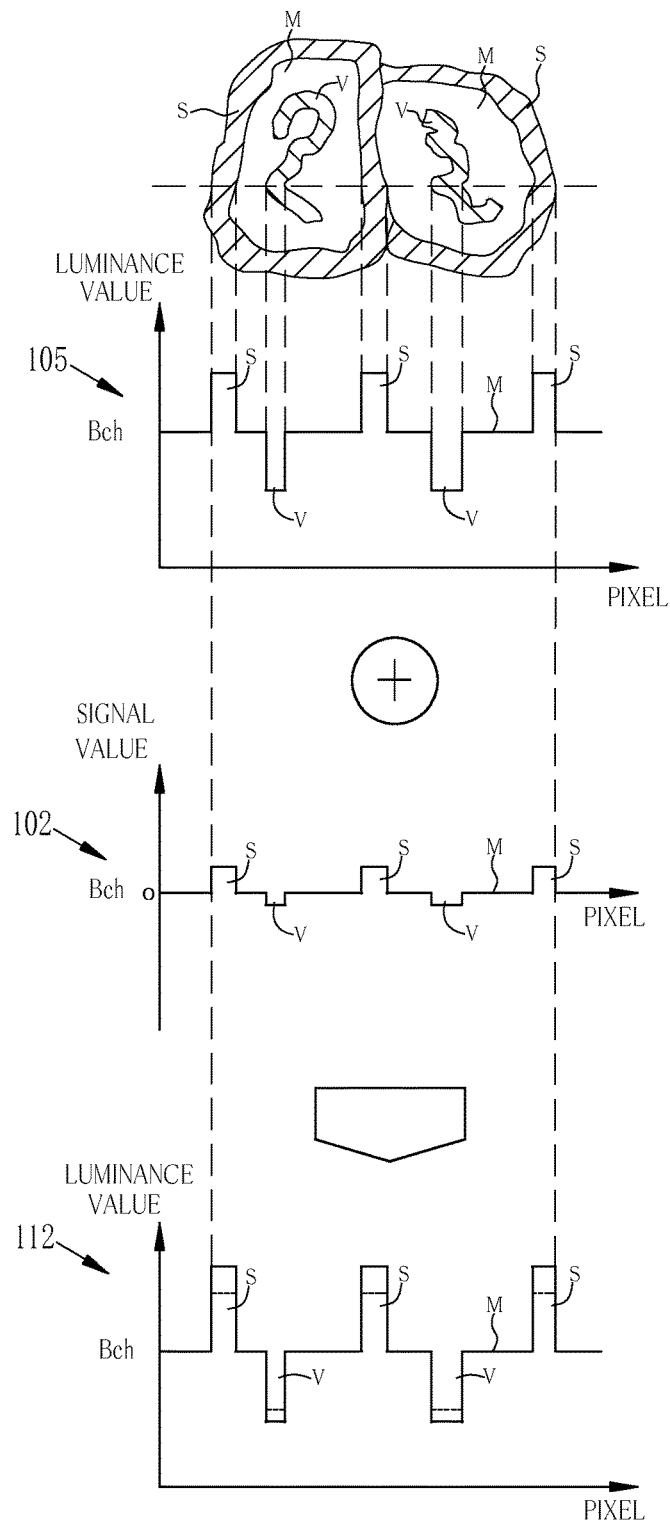
FIG. 13 is a graph illustrating luminance distribution in a display-controlled image obtained by combining the display controlling image in FIG. 10C with the base image.

Further, in the case where the display controlling image 101, in which the signal value of the pixel of the capillary vessels V is a negative value as shown in FIG. 9C, is combined with Bch of the base image 105, a display-controlled image 111, in which the contrast between the capillary vessels V and the surrounding mucous membrane M is increased as shown in FIG. 12, is obtained. Incidentally, dotted lines denote luminance values before the image composition, in the same manner as FIG. 11. Furthermore, in the case where the display controlling image 102, in which the signal value of the pixel of the ductal structure S is a positive value and the signal value of the pixel of the capillary vessels V is a negative value as shown in FIG. 10C, is combined with Bch of the base image 105, a display-controlled image 112, in which the contrast between the ductal structure S and the surrounding mucous membrane M and the contrast between the capillary vessels V and the surrounding mucous membrane M are increased as shown in FIG. 13, is obtained. Incidentally, dotted lines denote luminance values before the image composition, in the same manner as FIG. 11.

The image display signal generating section 66 converts a normal image inputted from the normal image processor 62 or a special image inputted from the special image processor 64 into a display image signal. Thereby, the normal image and the special images are displayable on the monitor 18. The monitor 18 displays the normal image or the special image based on the display image signal after the conversion.

Figure 14:
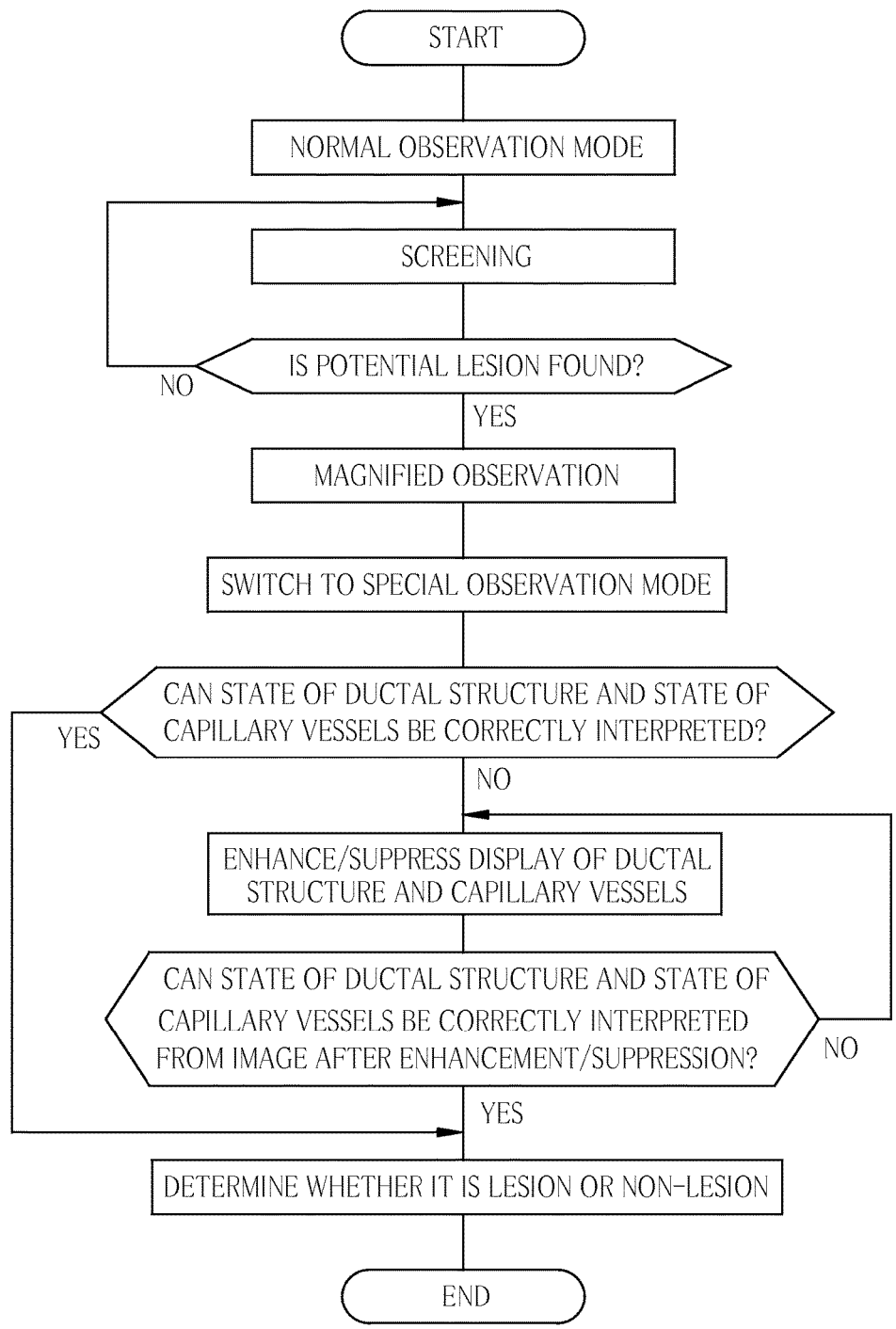
FIG. 14 is a flowchart illustrating a procedure in the first embodiment.

Next, a procedure of this embodiment is described using a flowchart shown in FIG. 14. First, in the normal observation mode, screening of the observation object is performed in a far view. In the case where a potential lesion that is a site with a potentially malignant lesion such as a brownish area or redness is detected in the screening, the zoom operation section 22c is operated to zoom in on the potential lesion. Thereby, magnified observation in which the potential lesion is magnified is performed. Concurrently, the mode selection SW 22b is operated to switch the mode to the special observation mode. Thereby, the special image is displayed on the monitor 18.

An operator observes the special image displayed on the monitor 18, and interprets the state of the ductal structure S and the state of the capillary vessels V, so as to determine whether or not the potential lesion is a lesion. In the case where the state of the ductal structure S and the state of the capillary vessels V are accurately interpreted from the special image, whether the potential lesion is a lesion or a non-lesion is determined based on the special image. In contrast, in the case where it is impossible to accurately interpret the state of the ductal structure S and the state of the capillary vessels V, the console 20 is operated to start up the setting menu screen as shown in FIG. 8A and the like. The sliders 97a and 98a are respectively operated on the "S" slide bar 97 and the "V" slide bar 98 in the setting menu screen, so as to enhance/suppress the display of the ductal structure S and the capillary vessels V in the special image.

In the case where the display of the capillary vessels V interferes in performing diagnoses based on observation of the ductal structure S, for example, the slider 97a is slid to the direction for enhancement on the "S" slide bar 97, and the slider 98a is slid to the direction for suppression on the "V" slide bar 98, as shown in FIG. 8A. Thereby, the special image in which the display of the ductal structure S is enhanced and the display of the capillary vessels V is suppressed is displayed on the monitor 18. The enhancement/depression of the display of the ductal structure S and the capillary vessels V is continuously performed until it becomes possible to accurately interpret the state of the ductal structure S and the state of the capillary vessels V.

Figure 15:
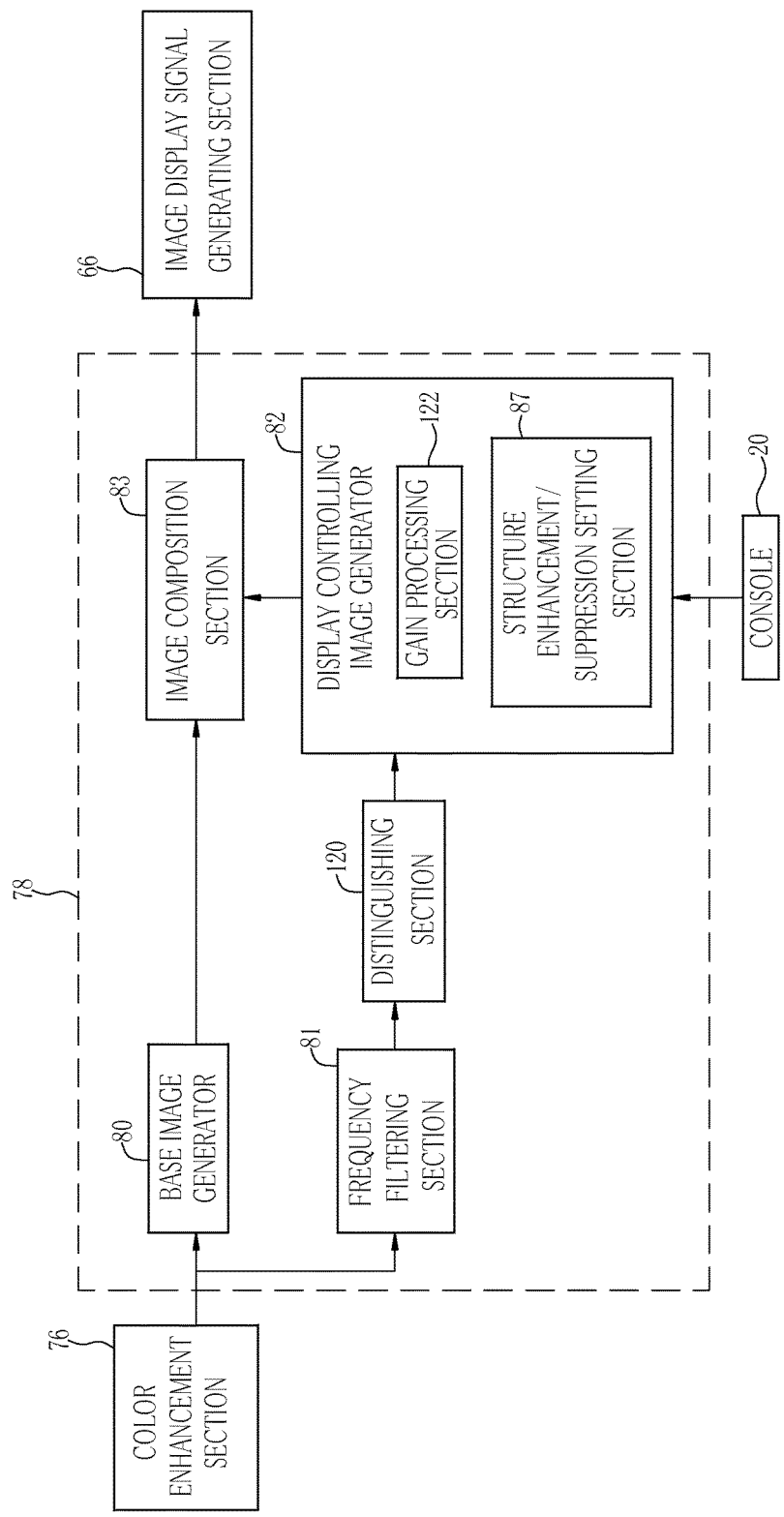
FIG. 15 is a block diagram illustrating each component in a structure enhancement/suppression section of another embodiment.

Note that, according to the first embodiment, the display controlling image is generated by inputting the entire structure-extracted image signal 85 to the display controlling image generator 82 without distinguishing between the rising edge and the falling edge in the structure-extracted image signal 85 which has been subjected to the frequency filtering process. However, the display controlling image may be generated by distinguishing between the rising edge and the falling edge in the structure-extracted image signal 85 and performing a gain process on the rising edge and the falling edge. For example, as shown in FIG. 15, a distinguishing section 120 is disposed between the frequency filtering section 81 and the display controlling image generator 82. The distinguishing section 120 determines the pixel having a positive value in the structure-extracted image signal 85 as a rising-edge pixel, and determines the pixel having a negative value in the structure-extracted image signal 85 as a falling-edge pixel. Then, a gain processing section 122 disposed in the display controlling image generator 82 performs the gain process corresponding to the enhancement degree or depression degree on the rising-edge pixel and the falling-edge pixel, so as to generate the display controlling image.

In this case, in order to enhance the display of the ductal structure S, the rising-edge pixel is subjected to the gain process for enhancement, so as to generate a display controlling image in which the rising-edge pixel has a positive value. In this case, as the enhancement degree becomes higher, the rising-edge pixel has a larger positive value. In order to suppress the display of the ductal structure S, the rising-edge pixel is subjected to the gain process for suppression, so as to generate a display controlling image in which the rising-edge pixel has a negative value. In this case, as the suppression degree becomes higher, the rising-edge pixel has a smaller negative value.

Further, in order to enhance the display of the capillary vessels V, the falling-edge pixel is subjected to the gain process for enhancement corresponding to the enhancement degree, so as to generate a display controlling image in which the falling-edge pixel has a negative value. In this case, as the enhancement degree becomes higher, the falling-edge pixel has a smaller negative value. In order to suppress the display of the capillary vessels V, the falling-edge pixel is subjected to the gain process for suppression corresponding to the suppression degree, so as to generate a display controlling image in which the falling-edge pixel has a positive value. In this case, as the suppression degree becomes higher, the falling-edge pixel has a larger positive value.

Furthermore, in order to enhance the display of both of the ductal structure S and the capillary vessels V and make the visual recognition of the capillary vessels V lower than that of the ductal structure S, the enhancement degree for the falling-edge pixel is made lower than that for the rising-edge pixel in performing the gain process for enhancement on the rising-edge pixel and the falling-edge pixel. In this case, an absolute value of the positive value of the rising-edge pixel is larger than an absolute value of the negative value of the falling-edge pixel in the display controlling image.

Second Embodiment

In the first embodiment, both the ductal structure S and the capillary vessels V are extracted by performing the frequency filtering process on the B image signal. In the second embodiment, the ductal structure S and the capillary vessels V are separately extracted by separately performing a frequency filtering process for ductal structure extraction on the B image signal and a frequency filtering process for blood vessel extraction on the B image signal. In light of the fact that the frequency band of the capillary vessels V is slightly closer to a high-frequency band in comparison with the frequency band of the ductal structure S, it is preferable that the frequency filtering process for ductal structure extraction and the frequency filtering process for blood vessel extraction are separately performed on the B image signal as with the second embodiment.

Figure 16:
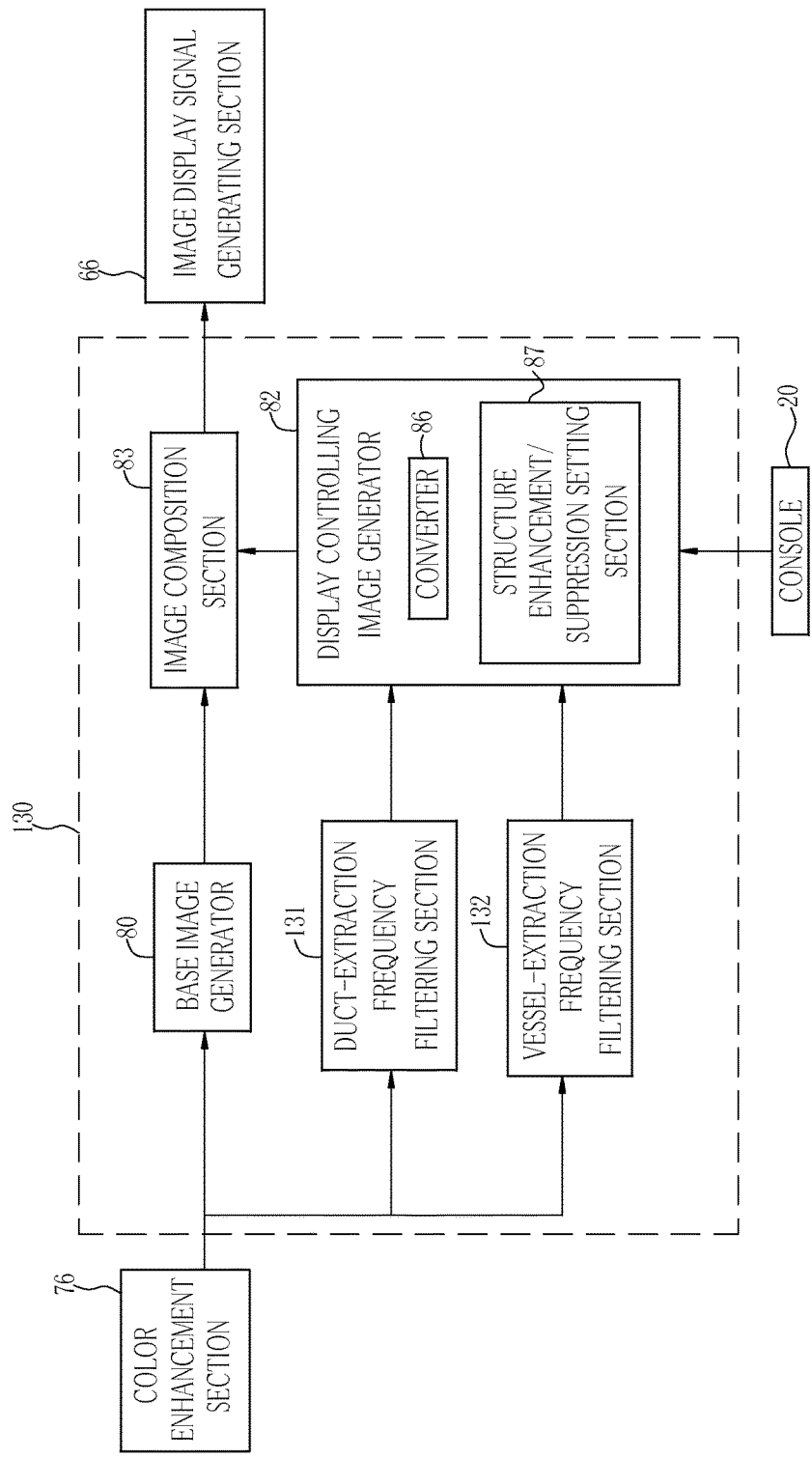
FIG. 16 is a block diagram illustrating each component in a structure enhancement/suppression section of a second embodiment.

In a structure enhancement/suppression section 130 of the second embodiment shown in FIG. 16, instead of the frequency filtering section 81 of the first embodiment, a duct-extraction frequency filtering section 131 and a vessel-extraction frequency filtering section 132 are disposed. Other than this, the configuration of the endoscope system of the second embodiment is substantially the same as that of the first embodiment.

In the duct-extraction frequency filtering section 131, the B image signal is subjected to the frequency filtering process for extracting a band containing a large area of the ductal structure S. Thus, a duct-extracted image signal obtained by extracting the ductal structure S is generated. The duct-extracted image signal is inputted to any one of the first converting section 90, the second converting section 91, and the fifth converting section 94 in the converter 86. In contrast, in the vessel-extraction frequency filtering section 132, the B image signal is subjected to the frequency filtering process for extracting a high-frequency band containing a large area of the capillary vessels V. Thus, a vessel-extracted image signal obtained by extracting the capillary vessels V is generated. The vessel-extracted image signal is inputted to anyone of the third converting section 92, the fourth converting section 93, and the sixth converting section 95 in the converter 86.

Third Embodiment

In the first embodiment, the display controlling image is combined with the base image so as to enhance/suppress the display of the ductal structure S and the display of the capillary vessels V. In the third embodiment, the display controlling image is combined with the base image so as to enhance the display of the ductal structure S or the display of the capillary vessels V, however, the base image is subjected to a blurring process so as to suppress the display of the ductal structure S or the display of the capillary vessels V.

Figure 17:
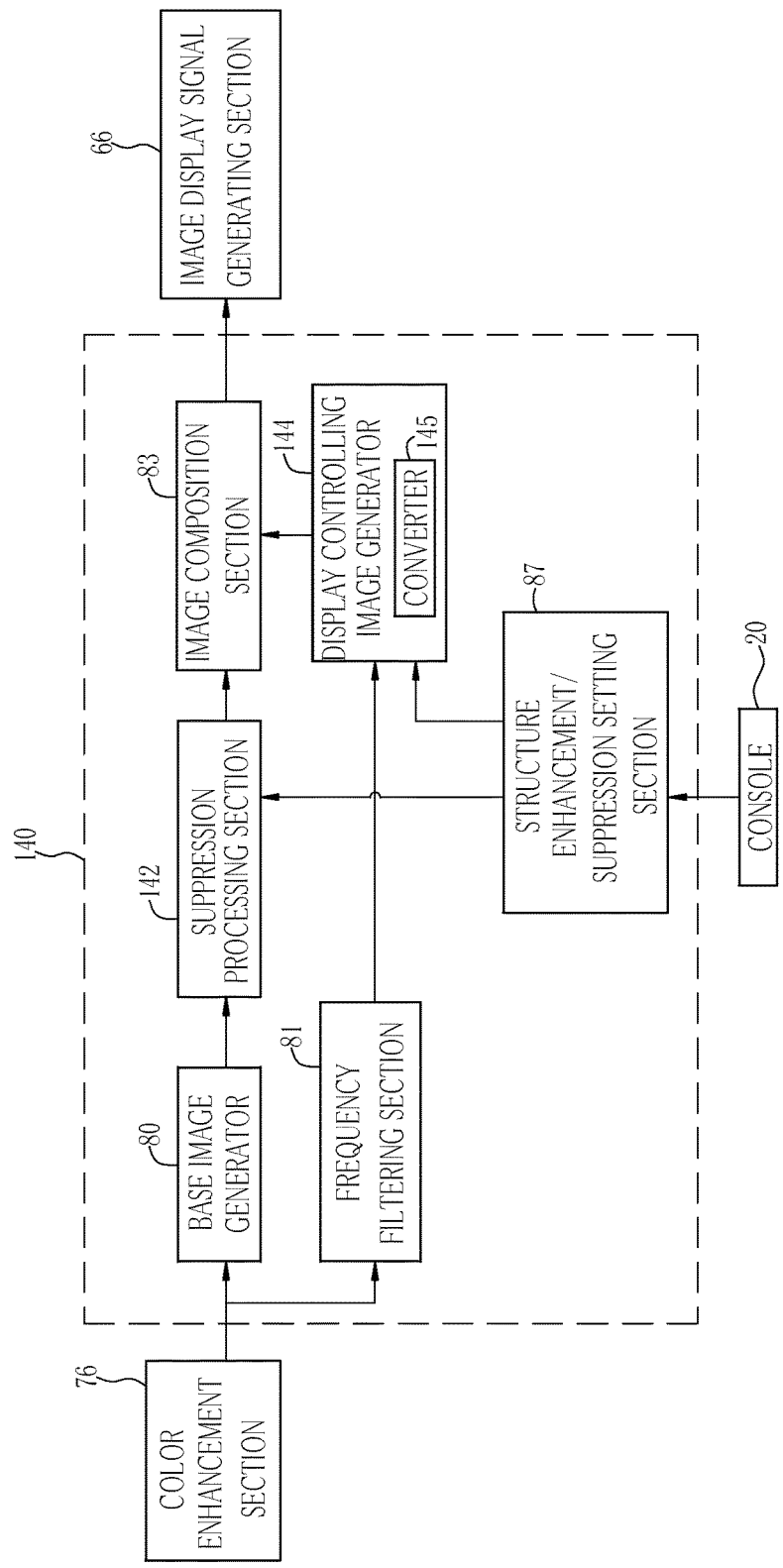
FIG. 17 is a block diagram illustrating each component in a structure enhancement/suppression section of a third embodiment.

In a structure enhancement/suppression section 140 of the third embodiment shown in FIG. 17, a suppression processing section 142 for blurring the base image is disposed between the base image generator 80 and the image composition section 83. Further, instead of the display controlling image generator 82 of the first embodiment, a display controlling image generator 144 for generating a display controlling image is disposed. Furthermore, the structure enhancement/suppression setting section 87 controls the suppression processing section 142 and the display controlling image generator 144 in accordance with the set enhancement/suppression conditions. Incidentally, other than those, the configuration of the endoscope system of the third embodiment is substantially the same as that of the first embodiment.

The suppression processing section 142 subjects the base image to the blurring process based on the suppression degree set by the structure enhancement/suppression setting section 87. As the suppression degree becomes higher, the blurring degree becomes higher. Incidentally, as the blurring process, low-pass filtering or the like is preferably used, for example. The display controlling image generator 144 includes a converter 145 to which the structure-extracted image signal 85 is inputted and from which the display controlling image is outputted. The converter 145 includes the first converting section 90, the third converting section 92, the fifth converting section 94, and the sixth converting section 95, but does not include the converting sections relating to the suppression (i.e., the second converting section 91 and the fourth converting section 93), unlike the converter 86.

According to the above first to third embodiments, a simultaneous method, in which plural image signals necessary for each observation mode are obtained simultaneously with a color image sensor, is employed to implement the present invention. Alternatively, a frame sequential method may be employed to implement the present invention. In the frame sequential method, plural image signals necessary for each observation mode are obtained sequentially with a monochrome image sensor.

Figure 18:
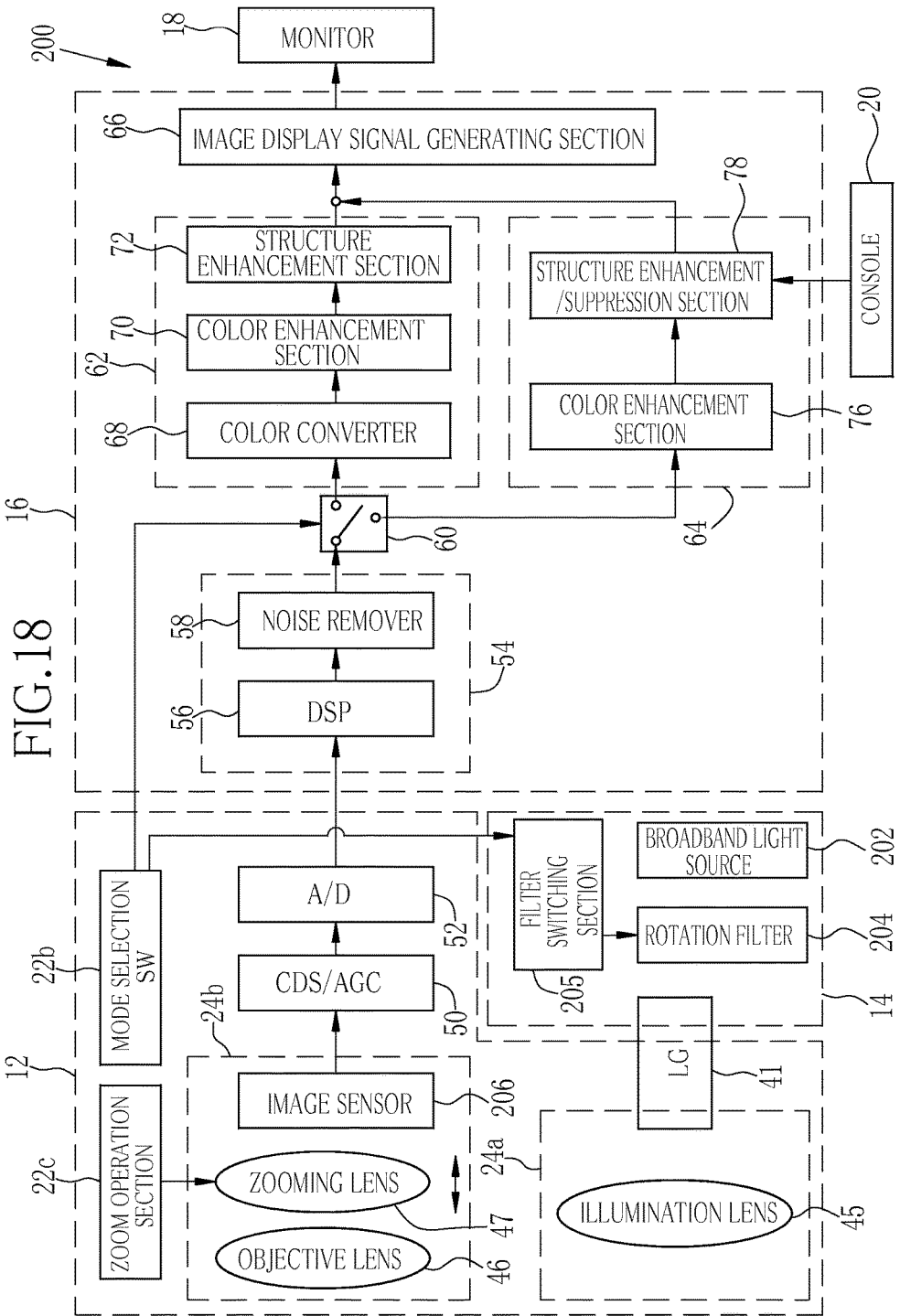
FIG. 18 is a block diagram illustrating each component in an endoscope system using a frame sequential method.

As shown in FIG. 18, the light source device 14 of an endoscope system 200 using the frame sequential method includes a broadband light source 202, a rotation filter 204, and a filter switching section 205, instead of the blue laser source 34, the blue-violet laser source 36, and the light source controller 40. The illuminating optical system 24a of the endoscope 12 is not provided with the phosphor 44. The imaging system 24b includes a monochrome image sensor 206 with no color filters, instead of the color image sensor 48. Other than those, the configuration of the endoscope system 200 is similar to the endoscope system 10 of the first embodiment.

The broadband light source 202 is a xenon lamp, a white LED, or the like, and emits the white light in a wavelength range from blue to red. The rotation filter 204 includes a normal observation mode filter 208 on its inner side and a special observation mode filter 209 on its outer side (see FIG. 19). The filter switching section 205 moves the rotation filter 204 in a radial direction thereof. In the case where the mode is set to the normal observation mode with use of the mode selection SW 22b, the filter switching section 205 inserts the normal observation mode filter 208 of the rotation filter 204 into a light path of the white light. In the case where the mode is set to the special observation mode with use of the mode selection SW 22b, the filter switching section 205 inserts the special observation mode filter 209 of the rotation filter 204 into the light path of the white light.

Figure 19:
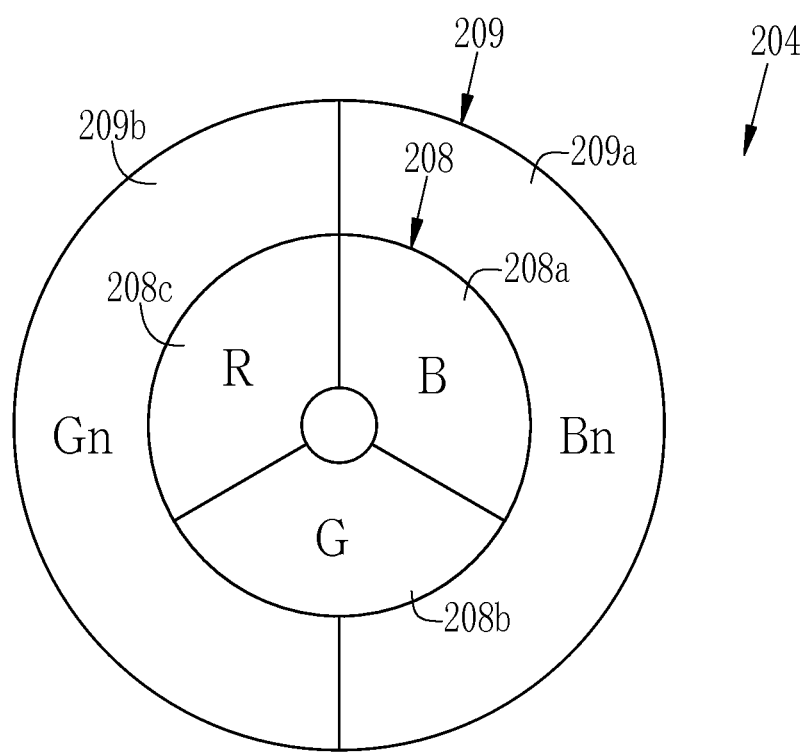
FIG. 19 is a plan view of a rotation filter.

As shown in FIG. 19, the normal observation mode filter 208 includes a B filter 208a, a G filter 208b, and an R filter 208c in a circumferential direction. The B filter 208a transmits blue light in the white light. The G filter 208b transmits green light in the white light. The R filter 208c transmits red light in the white light. Hence, in the normal observation mode, the blue light, the green light, and the red light are sequentially applied to the inside of the observation object as the rotation filter 204 is rotated.

The special observation mode filter 209 includes a Bn filter 209a and a Gn filter 209b in the circumferential direction thereof. The Bn filter 209a transmits blue narrowband light with the center wavelength of 415 nm in the white light. The Gn filter 209b transmits green narrowband light with the center wavelength of 540 nm in the white light. Hence, in the special observation mode, the blue narrowband light and the green narrowband light are alternately applied to the inside of the observation object as the rotation filter 204 is rotated. Consequently, in the endoscope system 200 using the frame sequential method, the broadband light source 202 and the Bn filter 209a of the rotation filter 204 constitute the narrow-band light source of the present invention.

The monochrome image sensor 206 of the endoscope system 200 using the frame sequential method captures an image of the inside of the observation object, every time the blue light, the green light, or the red light is applied to the inside of the observation object in the normal observation mode. Thereby, RGB image signals of three colors are obtained. The normal image is generated based on the RGB image signals, in a manner similar to that of the first embodiment.

In contrast, in the special observation mode, the monochrome image sensor 206 captures an image of the inside of the observation object, every time the blue narrowband light or the green narrowband light is applied to the inside of the observation object. Thereby, a Bn image signal and a Gn image signal are obtained. Based on the Bn image signal and the Gn image signal, the special image is generated. Unlike the first embodiment, the En image signal is assigned to the B image data and the G image data, and the Gn image signal is assigned to the R image data, so as to generate the base image. In order to generate the display controlling image, instead of the B image signal, the En signal is used. Other than those, the special image is generated in a manner similar to that of the first embodiment.

Note that, the phosphor 44 is provided in the distal portion 24 of the endoscope 12 in the first embodiment shown in FIG. 2. Instead, the phosphor 44 may be provided in the light source device 14. In this case, the phosphor 44 is preferably provided between the light guide 41 and the blue laser source 34.

Note that, the endoscope system 10 using the above-described simultaneous method uses the B image signal to generate the display-controlled image. The B image signal is a narrowband signal in which information of narrowband wavelengths of the blue laser beams and the blue-violet laser beams is included. The endoscope system 200 using the above-described frame sequential method uses the Bn image signal to generate the display-controlled image. The Bn image signal is a narrowband signal in which information of narrowband wavelength of the blue narrowband light is included. Instead, a blue narrowband image signal may be generated by spectral calculation based on a broadband image such as a white light image, to generate a display-controlled image. The blue narrowband image signal has a considerable amount of information related to the ductal structure S and the capillary vessels V.

Figure 20:
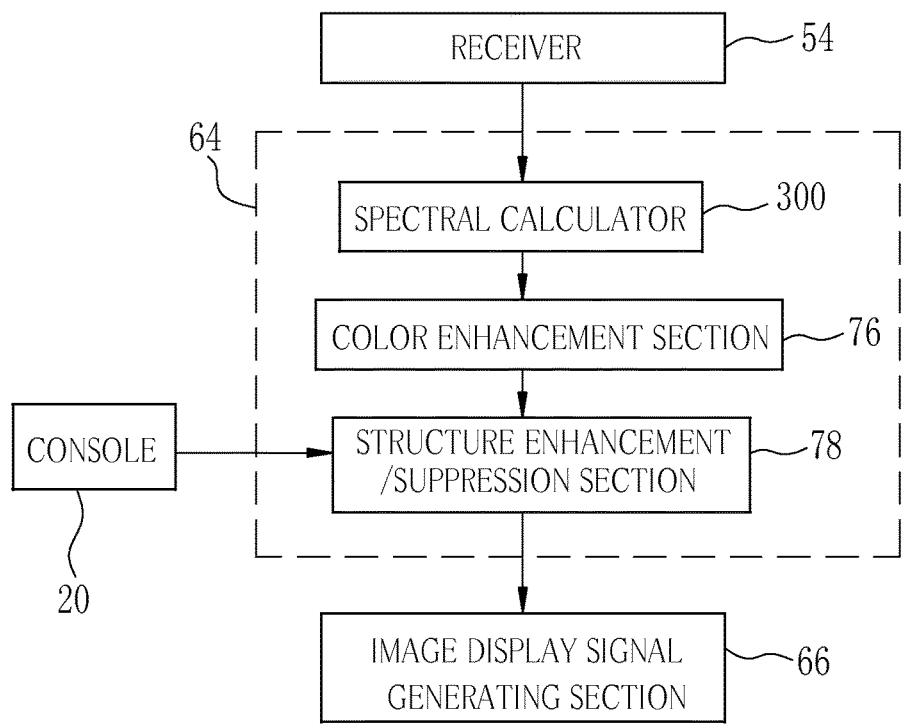
FIG. 20 is a block diagram of a special image processor having a spectral calculator.

In this case, in the special observation mode, the endoscope system 10 using the simultaneous method applies the white light as the broadband light instead of the special light. As shown in FIG. 20, a spectral calculator 300 is provided between the receiver 54 and the color enhancement section 76. The spectral calculator 300 performs a spectral calculation process based on the RGB image signals obtained by the image capturing with the illumination of the white light. Thereby, a blue narrowband image signal is generated. The blue narrowband image signal (for example, a blue narrowband image signal having information of wavelength of 415 nm) has a considerable amount of information related to the ductal structure S and the capillary vessels V. A method of the spectral calculation disclosed in Japanese Patent Laid-Open Publication No. 2003-093336 is used. The display-controlled image is generated based on the blue narrowband image signal, which is generated by the spectral calculator 300, and the G and R image signals, in steps similar to those in the above embodiments. Incidentally, as the white light, not only the white light obtained by the phosphor 44 but also the broadband light emitted from a broadband light source such as a xenon lamp may be used.

Note that, in the above embodiments, the image processing is performed during the observation using the endoscope. However, the present invention is not limited thereto. The image processing may be performed based on an endoscope image stored in a storage section of the endoscope system after the observation using the endoscope. Further, the image processing may be performed based on a capsule endoscope image captured by a capsule endoscope.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An image processing device comprising:
   an image signal generator for generating image signals of a plurality of colors by capturing an image of a mucous membrane surface;
   a base image generator for generating a base image based on the image signals of the plurality of colors, the base image containing a first structure having a luminance value higher than a luminance value of a mucous membrane;
   a structure-extracted image generator for generating a first structure-extracted image signal by subjecting a short-wavelength image signal containing a short-wavelength component out of the image signals of the plurality of colors to a first frequency component extracting process for extracting a first frequency component so as to extract a pixel of the first structure having a positive signal value;
   a display controlling image generator for generating a display controlling image to be used for display control of the first structure based on the first structure-extracted image signal; and
   an image compositor for generating a display-controlled image in which display of the first structure is controlled by combining the display controlling image with the base image to combine the first structure of the display controlling image with the first structure of the base image,
   wherein
   the structure-extracted image generator subjects the short-wavelength image signal to the first frequency component extracting process so as to generate the first structure-extracted image signal in which the pixel of the first structure having a positive signal value is extracted and a second structure-extracted image signal in which a pixel of a second structure having a negative signal value is extracted,
   the display controlling image generator generates a display controlling image to be used for display control of the first structure or the second structure based on the first and second structure-extracted image signals, and
   the image compositor generates a display-controlled image in which display of the first structure or the second structure is controlled by combining the display controlling image with the base image.

2. The image processing device of claim 1, wherein the short-wavelength image signal is a B image signal corresponding to a blue component.

3. The image processing device of claim 2, wherein the B image signal is a blue narrowband image signal.

4. The image processing device of claim 3, further comprising a narrow-band light source for emitting blue narrowband light, wherein
   the blue narrowband image signal is obtained by capturing an image of the mucous membrane surface illuminated with the blue narrowband light by the image signal generator.

5. The image processing device of claim 3, further comprising a spectral calculator for performing spectral calculation based on the image signals of the plurality of colors, wherein
   the blue narrowband image signal is obtained by the spectral calculation.

6. The image processing device of claim 1, further comprising a magnifying section for magnifying the mucous membrane surface, wherein
   the short-wavelength image signal is obtained in magnified observation using the magnifying section.

7. The image processing device of claim 1, wherein the display controlling image generator is equivalent to a converter for outputting a display controlling image in which the pixel of the first structure or the second structure has a value corresponding to a display control degree in response to an input of the first and second structure-extracted image signals.

8. The image processing device of claim 7, wherein the converter includes a first converting section for outputting a display controlling image in which the pixel of the first structure has a positive value corresponding to an enhancement degree so as to enhance display of the first structure.

9. The image processing device of claim 7, wherein the converter includes a second converting section for outputting a display controlling image in which the pixel of the first structure has a negative value corresponding to a suppression degree so as to suppress display of the first structure.

10. The image processing device of claim 7, wherein the converter includes a third converting section for outputting a display controlling image in which the pixel of the second structure has a negative value corresponding to an enhancement degree so as to enhance display of the second structure.

11. The image processing device of claim 7, wherein the converter includes a fourth converting section for outputting a display controlling image in which the pixel of the second structure has a positive value corresponding to a suppression degree so as to suppress display of the second structure.

12. The image processing device of claim 7, wherein the converter includes a specific converting section for outputting a display controlling image in which the pixel of the first structure has a positive value, the pixel of the second structure has a negative value, and an absolute value of the pixel value of the first structure is different from an absolute value of the pixel value of the second structure, so as to enhance display of both of the first and second structures and make a difference between visual recognition of the first structure and visual recognition of the second structure.

13. The image processing device of claim 1, further comprising:
a distinguishing section for determining a pixel value of each of the first and second structure-extracted image signals; and
a gain processing section for generating a display controlling image by performing a gain process corresponding to the display control degree of the first or second structure on the pixels of the first and second structure-extracted image signals each of which is determined to have a positive value or a negative value by the distinguishing section.

14. The image processing device of claim 13, wherein the gain processing section subjects the pixel determined to have a positive value and the pixel determined to have a negative value by the distinguishing section to a gain process for enhancement having a different enhancement degree corresponding to each of the pixels, so as to enhance display of both of the first and second structures and make a difference between the visual recognition of the first structure and the visual recognition of the second structure.

15. The image processing device of claim 1, further comprising a suppression processing section for subjecting the base image to a suppression process, wherein
the structure-extracted image generator subjects the short-wavelength image signal to the first frequency component extracting process, so as to generate the first structure-extracted image signal in which the pixel of the first structure having a positive signal value is extracted and a second structure-extracted image signal in which a pixel of a second structure having a negative signal value is extracted,
the display controlling image generator generates a display controlling image to be used to enhance display of a specific structure that is one of the first structure and the second structure based on the first and second structure-extracted image signals, and
the image compositor generates a display-controlled image in which display of the specific structure that is one of the first structure and the second structure is enhanced and display of the other of the first structure and the second structure is suppressed by combining the display controlling image with the base image which has been subjected to the suppression process.

16. The image processing device of claim 1, wherein the first structure is a ductal structure.

17. The image processing device of claim 1, wherein the first structure is a ductal structure and the second structure is capillary vessels.

18. A method for operating an endoscope system comprising:
an image signal generating step for generating image signals of a plurality of colors by capturing an image of a mucous membrane surface;
a base image generating step for generating a base image based on the image signals of the plurality of colors, the base image containing a first structure having a luminance value higher than a luminance value of a mucous membrane;
a structure-extracted image generating step for generating a first structure-extracted image signal by subjecting a short-wavelength image signal having a short-wavelength component out of the image signals of the plurality of colors to a first frequency component extracting process for extracting a first frequency component so as to extract a pixel of the first structure having a positive signal value;
a display controlling image generating step for generating a display controlling image to be used for display control of the first structure based on the first structure-extracted image signal; and
an image compositing step for generating a display-controlled image in which display of the first structure is controlled by combining the display controlling image with the base image to combine the first structure of the display controlling image with the first structure of the base image,
wherein
in the structure-extracted image generating step, the short-wavelength image signal is subjected to the first frequency component extracting process so as to generate the first structure-extracted image signal in which the pixel of the first structure having a positive signal value is extracted and a second structure-extracted image signal in which a pixel of a second structure having a negative signal value is extracted,
in the display controlling image generating step, a display controlling image is generated to be used for display control of the first structure or the second structure based on the first and second structure-extracted image signals, and
in the image compositing step, a display-controlled image is generated in which display of the first structure or the second structure is controlled by combining the display controlling image with the base image.

* * * * *